US012644127B2

(12) United States Patent
Petolino et al.

(10) Patent No.: US 12,644,127 B2
(45) Date of Patent: Jun. 2, 2026

(54) HAPLOID MAIZE TRANSFORMATION

(71) Applicant: CORTEVA AGRISCIENCE LLC, Indianapolis, IN (US)

(72) Inventors: Joseph F. Petolino, Zionsville, IN (US); Tonya L. Strange, Brownsburg, IN (US); Jayakumar Pon Samuel, Indianapolis, IN (US); Ryan C. Blue, Fishers, IN (US); Matthew A. Simpson, Brownsburg, IN (US)

(73) Assignee: CORTEVA AGRISCIENCE LLC, Indianapolis, IN (US)

( * ) Notice: Subject to any disclaimer, the term of this patent is extended or adjusted under 35 U.S.C. 154(b) by 298 days.

(21) Appl. No.: 14/695,434

(22) Filed: Apr. 24, 2015

(65) Prior Publication Data

US 2015/0307889 A1     Oct. 29, 2015

Related U.S. Application Data

(60) Provisional application No. 61/985,042, filed on Apr. 28, 2014.

(51) Int. Cl.
    *C12N 15/82* (2006.01)

(52) U.S. Cl.
    CPC ................................ *C12N 15/8213* (2013.01)

(58) Field of Classification Search
    CPC .................................................. C12N 15/8213
    See application file for complete search history.

(56) References Cited

U.S. PATENT DOCUMENTS

| | | | | |
|---|---|---|---|---|
| 5,602,310 | A * | 2/1997 | Petolino | A01H 4/00 |
| | | | | 800/320.1 |
| 7,572,635 | B2 | 8/2009 | Armstrong et al. | |
| 2002/0023278 | A1* | 2/2002 | Lyznik | A01H 1/02 |
| | | | | 800/278 |
| 2007/0107077 | A1 | 5/2007 | Chen et al. | |
| 2009/0133152 | A1 | 5/2009 | Lyznik et al. | |
| 2010/0218281 | A1* | 8/2010 | Trolinder | C12Q 1/6895 |
| | | | | 435/6.12 |
| 2011/0203012 | A1* | 8/2011 | Dotson | C12N 15/829 |
| | | | | 800/278 |
| 2013/0198893 | A1* | 8/2013 | Zhao | C12N 15/8201 |
| | | | | 800/278 |
| 2015/0150160 | A1* | 5/2015 | Sanchez-Fernandez | ...................... |
| | | | | C12N 15/902 |
| | | | | 435/468 |
| 2015/0307889 | A1 | 10/2015 | Petolino et al. | |

FOREIGN PATENT DOCUMENTS

| | | | | |
|---|---|---|---|---|
| WO | | 2007055687 | A1 | 5/2007 | |
| WO | | WO-2013169802 | A1 * | 11/2013 | ........... C12N 15/102 |

OTHER PUBLICATIONS

Djukanovic et al (Gene conversion in transgenic maize plants expressing FLP/FRT and Cre/loxP site-specific recombination system. Plant Biotechnology Journal. 4, 345-357, 2006).*
Vega et al (Agrobacterium-mediated transformation of maize (Zea mays) with Cre-lox site specific recombination cassettes in BIBAC vectors. Plant Mol Biol 66:587-598, 2008).*
Francois et al (Engineering the haploid genome of microspores. Biocatalysis and Agricultural Biotechnology 3:20-23, Jan. 2014).*
Martin et al (The Order of Strand Exchanges in Cre-LoxP Recombination and its Basis Suggested by the Crystal Structure of a Cre-LoxP Holliday Junction Complex. J Mol Biol. 24; 319(1): 107-127, 2002).*
Sengupta et al (Viral Cre-LoxP tools aid genome engineering in mammalian cells. Journal of Biological Engineering. 11:45, 1-9, 2017).*
Shukla et al (Precise genome modification in the crop species Zea mays using zinc-finger nucleases. Nature. vol. 459: 437-443, 2009) (Year: 2009).*
Francois et al (Engineering the haploid genome of microspores. Biocatalysis and Agricultural Biotechnology 3:20-23, Jan. 2014) (Year: 2014).*
Fennell et al (Electroporation and PEG delivery of DNA into maize microspores. Plant Cell Reports. 11:567-570, 1992). (Year: 1992).*
Mitchell et al (Plant Regeneration from Haploid Suspension and Protoplast Cultures from Isolated Microspores of Maize. J. Plant Physiol. vol. 137: 530-536, 1991). (Year: 1991).*
Wan et al (I callus as a bombardment target for generating fertile transgenic maize (Zea mays L.). Planta. 196:7-14, 1995) (Year: 1995).*
Gurushidze et al (True-Breeding Targeted Gene Knock-Out in Barley Using Designer TALE-Nuclease in Haploid Cells. PLOS ONE. p. 1-9, Mar. 2014) (Year: 2014).*
Wan et al (callus as a bombardment target for generating fertile transgenic maize (Zea mays L.). Planta. 196:7-14, 1995) (Year: 1995).*
Murove et al (Chapter 5. Haploids and Doubled Haploids in Plant Breeding. Plant breeding. p. 87-106, 2012). (Year: 2012).*
Chair et al (Transformation of haploid, microspore-derived cell suspension protoplasts of rice (Oryza sativa L.). Plant cell Reports, p. 766-770, 1996). (Year: 1996).*
Yang et al (Contributions of Zea mays subspecies Mexicana haplotypes to modern maize. Nature Communication. p. 1-10, Nov. 2017) (Year: 2017).*
Zhu et al (Efficiency and Inheritance of Targeted Mutagenesis in Maize Using CRISPR-Cas9. Journal of Genetics and Genomics p. 25-36, 2016) (Year: 2016).*

(Continued)

*Primary Examiner* — Wayne Zhong

(57) ABSTRACT

Disclosed are methods for transformation of an androgenic-derived, haploid cell line with a site-specific nuclease. In some embodiments, the androgenic-derived, haploid cell line is a maize microspore-derived plant tissue culture. In addition, the disclosure provides a method for modifying, e.g., by mutating or targeting and integrating donor DNA into a specific locus of a haploid or dihaploid tissue genome. The disclosure further provides methods for regenerating a whole plant from the haploid or dihaploid tissue that contains either the mutation at a specific genomic locus or a donor DNA integrated within a specific genomic locus may be obtained from the subject disclosure.

12 Claims, 5 Drawing Sheets

Specification includes a Sequence Listing.

(56)        References Cited

OTHER PUBLICATIONS

Javaid et al (CRISPR/Cas System and Factors Affecting Its Precision and Efficiency. Frontiers in Cell and Developmental Biology. p. 1-25, 2021) (Year: 2021).*

Wusheng, Jiang; et al.: "Study on Maize Haploid Induction and Gene Gun Transformation," National Crops Cell and Molecular Breeding Syposium Proceedings, Mar. 31, 2003 (Mar. 31, 2003), pp. 373-378.

Aulinger et al., Gametic embryos of maize as a target for biolistic transformation: comparison to immature zygotic embryos, Plant Cell Rep (2002) 21:585-591.

Belhaj et. al., Plant genome editing made easy: targeted mutagenesis in model and crop plants using the CRISPR/CAS system, Plant Methods, (2013) 9:39.

Chen, K. et al., Targeted genome modification technologies and their applications in crop improvements, Plant Cell Rep (2014) 33:575-583.

Djukanovic et al., Gene conversion intransgenic maize plants expressing FLP/FRT and Cre/loxP site-specific recombinations systems, (2006) Plant Biotech. J. 4:345-357.

Extended European Search Report, dated Nov. 2, 2017 for EP Counterpart Application No. 15785964.

Folling et al, Transformation of wheat (*Triticum aestivum* L.) microspore-derived callus and microspores by particle bombardment, Plant Cell Rep (2001) 20:629-636.

He et al., An improved system to establish highly embryogenic haploid cell and protoplast cultures from pollen calluses of maize (*Zea mays* L.), Plant Cell, Tissue and Organ Culture (2006) 86:15-25.

Sukhapinda K. et al, Transformation of Maize (*Zea mays* L.) protoplasts and regeneration of haploid transgenic plants, 1993, Plant Cell Reports, (1993) 13:63-68.

Xie et al., RNA-Guided Genome Editing in Plants using CRISPR-CAS System, Molecular Plant, (2013) pp. 6(6) 1975-1983.

Zhang, Y., et al., Transcription Activator-Like Effector Nucleases Enable Efficient Plant Genome Engineering, Plant Physiology, 2013, 161:20-27.

Aulinger I.E., et al., "Gametic Embryos of Maize as a Target for Biolistic Transformation: Comparison to Immature Zygotic Embryos," Plant Cell Reports, 2003, vol. 21, pp. 585-591, 8 Pages, E Published on 2002.

Belhaj K., et al. "Plant Genome Editing Made Easy: Targeted Mutagenesis in Model and Crop Plants Using the CRISPR/Cas System," Plant Methods, Oct. 2013, vol. 9, pp. 1-10.

Chen K., et al., "Targeted Genome Modification Technologies and their Applications in Crop Improvements," Plant Cell Reports, Springer International, DE, Apr. 1, 2004, vol. 33, No. 4, pp. 575-583, DOI: 10.1007/S00299-013-1539-6, ISSN 0721-7714, XP002742322, EPublished on Nov. 24, 2013.

Djukanovic V., et al., "Gene Conversion in Transgenic Maize Plants Expressing FLP/FRT and Cre/loxP Site-Specific Recombinations Systems," Plant Biotechnology Journal, 2006, vol. 4, pp. 345-357.

Extended European Search Report for European Application No. 15785964.6, mailed Nov. 2, 2017, 8 Pages.

Fennell A., et al., "Electroporation and PEG Delivery of DNA into Maize Microspores," Plant Cell Reports, 1992, vol. 11, pp. 567-570.

Folling L., et al.,"Transformation of Wheat (*Triticum aestivum* L. ) Microspore-Derived Callus and Microspores by Particle Bombardment," Plant Cell Reports, 2001, vol. 20, pp. 629-636.

Francois E., et al., "Engineering the Haploid Genome of Microspores," Biocatalysis and Agricultural Biotechnology, Jan. 2014, vol. 3, pp. 20-23.

Gurushidze M., et al., "True-Breeding Targeted Gene Knock-Out in Barley Using Designer TALE-Nuclease in Haploid Cells," PLOS ONE, Mar. 2014, vol. 9, No. 3, e92046, 9 pages.

He G., et al., "An Improved System to Establish Highly Embryogenic Haploid Cell and Protoplast Cultures from Pollen Calluses of Maize (*Zea mays* L.)," Plant Cell, Tissue and Organ Culture, Kluwer Academic Publishers, DO, Apr. 5, 2006, vol. 86, No. 1, pp. 15-25, doi: 10.1007/S11240-006-9091-5, ISSN 1573-5044, XP019409352.

International Preliminary Report on Patentability for International Application No. PCT/US2015/027484, mailed Nov. 10, 2016, 6 Pages.

International Search Report and Written Opinion for International Application No. PCT/US2015/027484, mailed Jul. 24, 2015, 9 Pages.

Martin S., et al., "The Order of Strand Exchanges in Cre-LoxP Recombination and its Basis Suggested by the Crystal Structure of a Cre-LoxP Holliday Junction Complex," Journal of Molecular Biology, May 24, 2002, vol. 319, No. 1, pp. 107-127, 35 Pages.

Mitchell J.C., et al., "Plant Regeneration from Haploid Suspension and Protoplast Cultures from Isolated Microspores of Maize," The Journal of Plant Physiology, 1991, vol. 137, pp. 530-536.

Sengupta R., et al., "Viral Cre-LoxP Tools Aid Genome Engineering in Mammalian Cells," Journal of Biological Engineering, 2017, vol. 11, No. 45, pp. 1-9.

Shukla V.K., et al., "Precise Genome Modification in the Crop Species *Zea mays* Using Zinc-finger Nucleases," Nature, May 21, 2009, vol. 459, No. 7245, pp. 437-441.

Sukhapinda K., et al., "Transformation of Maize (*Zea mays* L.) Protoplasts and Regeneration of Haploid Transgenic Plants, "Plant Cell Reports, 1993, vol. 13, No. 2, pp. 63-68, 4 pages, ISSN 0721-7714, XP009500725.

Vega J.M., et al., "Agrobacterium-Mediated Transformation of Maize (*Zea mays*) with Cre-Lox Site Specific Recombination Cassettes in BIBAC Vectors," Plant Molecular Biology, 2008, vol. 66, pp. 587-598.

Wan, et al., "Type I callus as a bombardment target for generating fertile transgenic maize" (*Zea mays* L.). Planta. 196: 1995, pp. 7-14.

Wusheng J., et al., "Research on Maize Haploid Embryo Induction and Biolistic Transformation," Proceedings of the National Symposium on Crop Cell Engineering and Molecular Technology Breeding, 2003 pp. 373-378.

Wusheng J., et al., "Study on Maize Haploid Embryo Induction and Gene Gun Transformation," National Crops Cell anc Molecular Breeding Syposium Proceedings, Mar. 31, 2003, pp. 373-378, 19 Pages.

Xie K., et al., "RNA-Guided Genome Editing in Plants Using a CRISPR-Cas System," Molecular Plant, Nov. 2013, vol. 6, No. 6, pp. 1975-1983.

Zhang Y., et al., "Transcription Activator-Like Effector Nucleases Enable Efficient Plant Genome Engineering 1[W] [OA]," Plant Physiology, Nov. 2, 2012, vol. 161, No. 1, pp. 20-27, DOI: 10.1104/pp. 112.205179, ISSN 0032-0889, XP055070911.

* cited by examiner

SEQ ID NO:32    GCTACGTGCCTTCGCATACGGAGTAGTTTATTCGCGGTGGGACACTTGATAGAGAAAGGCTACGGTAGCGTACTTCTA

SEQ ID NO:33    CTACGTGCCTTCGCATACGGAGT--------TTCGCGGTGGGACACTTGATAGAGAAAGGCTACGGTAGCGTACTTCTA

SEQ ID NO:34    CTACGTGCCTTCGCATACGGAGT---------TTCGtGGTGGGACACTTGATAGAAAGGCTACGGTAGCGTACTTCTA

SEQ ID NO:35    CTACGTGCCTTCGCATACGGAG---------TATTCGCGGTGGGACACTTGATAGAAAGGCTACGGTAGCGTACTTC-A

SEQ ID NO:36    TACGTGCCTTCGCATACGGAGTAG-------gCGCGGTGGGACACTTGATAGAAAGGCTACGGTAGCGTACTTCTA

SEQ ID NO:37    TACGTGCCTTCGCATACGGAG---------TATTCGCGGTGGGACACTTGATAGAAAGGCTACGGTAGCGTACTTCTA

SEQ ID NO:38    TACGTGCCTTCGCATACGGAG-------TcATTCGCGGTGGGACACTTGATAGAAAGGCTACGGTAGCGTACTTCT-

SEQ ID NO:39    TACGTGCCTTCGCATACGGAGT---------TTCGCGGTGGGACACTTGATAGAAAGGCTACGGTAGCGTACTTCTA

SEQ ID NO:40    TACGTGCCTTCGCATACGGAG--------TcATTCGCGGTGGGACACTTGATAGAAAGGCTACGGTAGCGTAC-TCTA

SEQ ID NO:41    ACGTGCCTTCGCATACGGAG--------TcATTCGCGGTGGGACACTTGATAGAAAGGCTACGGTAGCGTACTTCTA

SEQ ID NO:42    ACGTGCCTTCGCATACGGAGTAG--------gCGCGGTGGGACACTTGATAGAAAGGCTACGGTAGCGTACTTCTA

SEQ ID NO:43    ACGTGCCTTCGCATACGGAG---------TATTCGCGGTGGGACACTTGATAGAAAGGCTACGGTAGCGTACTTCTA

SEQ ID NO:44    CGTGCCTTCGCATACGGAGTAGT-----TTCGCGGTGGGACACTTGATAGAGAAAGGCTACGGTAGCGTACTTCTA

SEQ ID NO:45    CGTGCCTTCGCATACGGAGTAG---------gCGCGGTGGGACACTTGATAGAGAAAGGCTACGGTAGCGTACTTCTA

FIGURE 4

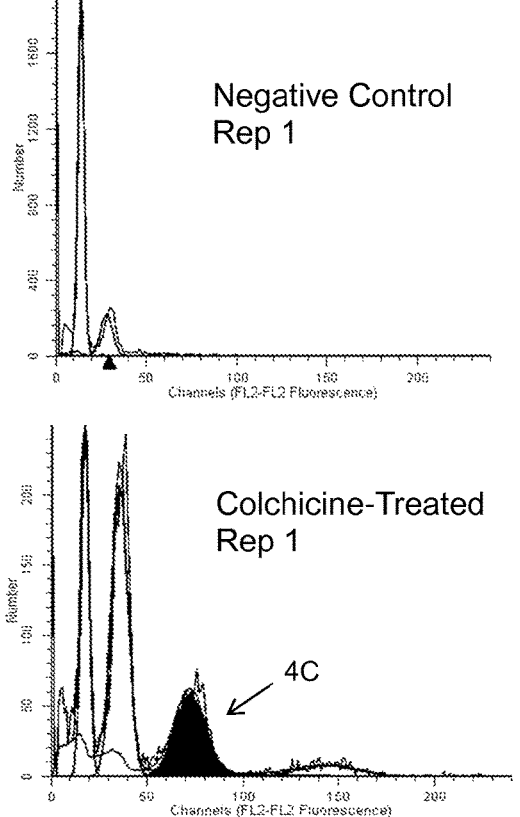
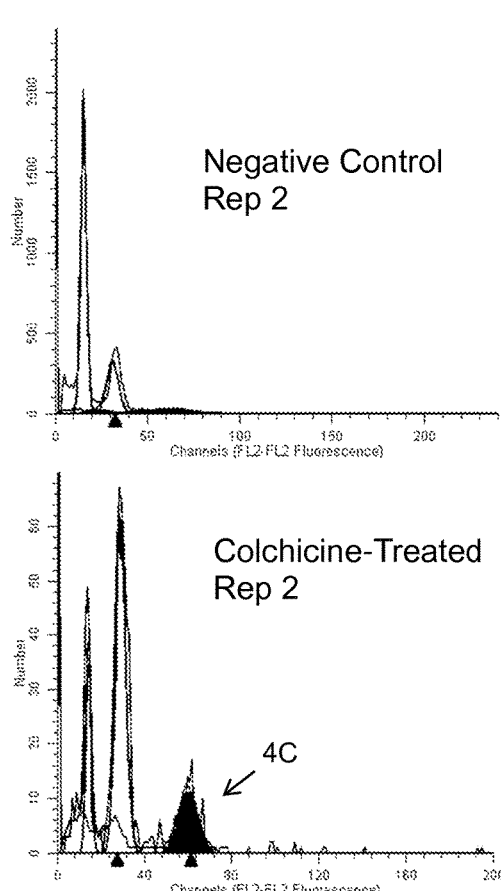
FIGURE 5

SEQUENCE LISTING

```
<160> NUMBER OF SEQ ID NOS: 45

<210> SEQ ID NO 1
<211> LENGTH: 18
<212> TYPE: DNA
<213> ORGANISM: artificial sequence
<220> FEATURE:
```

-continued

```
<223> OTHER INFORMATION: ZFP monomer

<400> SEQUENCE: 1
actccgtatg cgaaggca                                                18

<210> SEQ ID NO 2
<211> LENGTH: 18
<212> TYPE: DNA
<213> ORGANISM: artificial sequence
<220> FEATURE:
<223> OTHER INFORMATION: ZFP Monomer

<400> SEQUENCE: 2
ttcgcggtgg gacacttg                                                18

<210> SEQ ID NO 3
<211> LENGTH: 21
<212> TYPE: DNA
<213> ORGANISM: Artificial Sequence
<220> FEATURE:
<223> OTHER INFORMATION: primer

<400> SEQUENCE: 3
cgccacaaat ctgaaccagc a                                            21

<210> SEQ ID NO 4
<211> LENGTH: 24
<212> TYPE: DNA
<213> ORGANISM: artificial sequence
<220> FEATURE:
<223> OTHER INFORMATION: primer

<400> SEQUENCE: 4
ccacgatcga cattgatctg gcta                                         24

<210> SEQ ID NO 5
<211> LENGTH: 21
<212> TYPE: DNA
<213> ORGANISM: artificial sequence
<220> FEATURE:
<223> OTHER INFORMATION: primer

<400> SEQUENCE: 5
ccagcataca gttagggccc a                                            21

<210> SEQ ID NO 6
<211> LENGTH: 20
<212> TYPE: DNA
<213> ORGANISM: artificial sequence
<220> FEATURE:
<223> OTHER INFORMATION: primer

<400> SEQUENCE: 6
gttgccttgg taggtccagc                                              20

<210> SEQ ID NO 7
<211> LENGTH: 21
<212> TYPE: DNA
<213> ORGANISM: artificial sequence
<220> FEATURE:
<223> OTHER INFORMATION: primer

<400> SEQUENCE: 7
gcgacatatc aggccaacag g                                            21
```

-continued

```
<210> SEQ ID NO 8
<211> LENGTH: 25
<212> TYPE: DNA
<213> ORGANISM: artificial sequence
<220> FEATURE:
<223> OTHER INFORMATION: primer

<400> SEQUENCE: 8
gggatatgtg tcctaccgta tcagg                                      25

<210> SEQ ID NO 9
<211> LENGTH: 21
<212> TYPE: DNA
<213> ORGANISM: artificial sequence
<220> FEATURE:
<223> OTHER INFORMATION: primer

<400> SEQUENCE: 9
cgaaaactca gcatgcggga a                                          21

<210> SEQ ID NO 10
<211> LENGTH: 21
<212> TYPE: DNA
<213> ORGANISM: artificial sequence
<220> FEATURE:
<223> OTHER INFORMATION: primer

<400> SEQUENCE: 10
gagccatcag tccaacactg c                                          21

<210> SEQ ID NO 11
<211> LENGTH: 26
<212> TYPE: DNA
<213> ORGANISM: artificial sequence
<220> FEATURE:
<223> OTHER INFORMATION: primer

<400> SEQUENCE: 11
tacgtatggc actaatctca ccggct                                     26

<210> SEQ ID NO 12
<211> LENGTH: 28
<212> TYPE: DNA
<213> ORGANISM: artificial sequence
<220> FEATURE:
<223> OTHER INFORMATION: primer

<400> SEQUENCE: 12
tacgtaagtc ttagaagtac gctaccgt                                   28

<210> SEQ ID NO 13
<211> LENGTH: 26
<212> TYPE: DNA
<213> ORGANISM: artificial sequence
<220> FEATURE:
<223> OTHER INFORMATION: primer

<400> SEQUENCE: 13
acgtactggc actaatctca ccggct                                     26

<210> SEQ ID NO 14
<211> LENGTH: 28
<212> TYPE: DNA
<213> ORGANISM: artificial sequence
<220> FEATURE:
<223> OTHER INFORMATION: primer
```

<400> SEQUENCE: 14
acgtacagtc ttagaagtac gctaccgt                                    28

<210> SEQ ID NO 15
<211> LENGTH: 20
<212> TYPE: DNA
<213> ORGANISM: artificial sequence
<220> FEATURE:
<223> OTHER INFORMATION: primer

<400> SEQUENCE: 15
tgttcggttc cctctaccaa                                             20

<210> SEQ ID NO 16
<211> LENGTH: 22
<212> TYPE: DNA
<213> ORGANISM: artificial sequence
<220> FEATURE:
<223> OTHER INFORMATION: primer

<400> SEQUENCE: 16
caacatccat caccttgact ga                                          22

<210> SEQ ID NO 17
<211> LENGTH: 24
<212> TYPE: DNA
<213> ORGANISM: artificial sequence
<220> FEATURE:
<223> OTHER INFORMATION: primer

<400> SEQUENCE: 17
cacagaaccg tcgcttcagc aaca                                        24

<210> SEQ ID NO 18
<211> LENGTH: 18
<212> TYPE: DNA
<213> ORGANISM: artificial sequence
<220> FEATURE:
<223> OTHER INFORMATION: primer

<400> SEQUENCE: 18
tggcggacga cgacttgt                                               18

<210> SEQ ID NO 19
<211> LENGTH: 19
<212> TYPE: DNA
<213> ORGANISM: artificial sequence
<220> FEATURE:
<223> OTHER INFORMATION: primer

<400> SEQUENCE: 19
aaagtttgga ggctgccgt                                              19

<210> SEQ ID NO 20
<211> LENGTH: 26
<212> TYPE: DNA
<213> ORGANISM: artificial sequence
<220> FEATURE:
<223> OTHER INFORMATION: primer

<400> SEQUENCE: 20
cgagcagacc gccgtgtact tctacc                                      26

<210> SEQ ID NO 21
<211> LENGTH: 20

-continued

```
<212> TYPE: DNA
<213> ORGANISM: artificial sequence
<220> FEATURE:
<223> OTHER INFORMATION: primer

<400> SEQUENCE: 21
aagcggtgcg ttggtattag                                           20

<210> SEQ ID NO 22
<211> LENGTH: 17
<212> TYPE: DNA
<213> ORGANISM: artificial sequence
<220> FEATURE:
<223> OTHER INFORMATION: primer

<400> SEQUENCE: 22
gcgtttaaca ggctggc                                              17

<210> SEQ ID NO 23
<211> LENGTH: 21
<212> TYPE: DNA
<213> ORGANISM: artificial sequence
<220> FEATURE:
<223> OTHER INFORMATION: primer

<400> SEQUENCE: 23
cgatgctcac cctgttgttt g                                         21

<210> SEQ ID NO 24
<211> LENGTH: 17
<212> TYPE: DNA
<213> ORGANISM: artificial sequence
<220> FEATURE:
<223> OTHER INFORMATION: primer

<400> SEQUENCE: 24
tcgcatacga cgggcat                                              17

<210> SEQ ID NO 25
<211> LENGTH: 30
<212> TYPE: DNA
<213> ORGANISM: artificial sequence
<220> FEATURE:
<223> OTHER INFORMATION: primer

<400> SEQUENCE: 25
ataagacatc gagctagtgt aagcgtaggc                                30

<210> SEQ ID NO 26
<211> LENGTH: 28
<212> TYPE: DNA
<213> ORGANISM: artificial sequence
<220> FEATURE:
<223> OTHER INFORMATION: primer

<400> SEQUENCE: 26
tcacaactgt ttaggcgtgt cctcttaa                                  28

<210> SEQ ID NO 27
<211> LENGTH: 27
<212> TYPE: DNA
<213> ORGANISM: artificial sequence
<220> FEATURE:
<223> OTHER INFORMATION: primer

<400> SEQUENCE: 27
```

-continued aaagctgcag ctgcctgttc cctgtac                                                    27

<210> SEQ ID NO 28
<211> LENGTH: 26
<212> TYPE: DNA
<213> ORGANISM: artificial sequence
<220> FEATURE:
<223> OTHER INFORMATION: primer

<400> SEQUENCE: 28
caaataagac atcgagctag tgtaag                                                     26

<210> SEQ ID NO 29
<211> LENGTH: 20
<212> TYPE: DNA
<213> ORGANISM: artificial sequence
<220> FEATURE:
<223> OTHER INFORMATION: primer

<400> SEQUENCE: 29
ctgtttaggc gtgtcctctt                                                            20

<210> SEQ ID NO 30
<211> LENGTH: 17
<212> TYPE: DNA
<213> ORGANISM: artificial sequence
<220> FEATURE:
<223> OTHER INFORMATION: primer

<400> SEQUENCE: 30
tcgcatacga cgggcat                                                               17

<210> SEQ ID NO 31
<211> LENGTH: 15
<212> TYPE: DNA
<213> ORGANISM: artificial sequence
<220> FEATURE:
<223> OTHER INFORMATION: primer

<400> SEQUENCE: 31
tggcagccgg tgcga                                                                 15

<210> SEQ ID NO 32
<211> LENGTH: 76
<212> TYPE: DNA
<213> ORGANISM: Artificial sequence
<220> FEATURE:
<223> OTHER INFORMATION: Genomic DNA recognition target sequence

<400> SEQUENCE: 32
gctacgtgcc ttcgcatacg gagtagttta ttcgcggtgg gacacttgat agaaaggcta    60
cggtagcgta cttcta                                                               76

<210> SEQ ID NO 33
<211> LENGTH: 69
<212> TYPE: DNA
<213> ORGANISM: artificial sequence
<220> FEATURE:
<223> OTHER INFORMATION: INDELS as a result of ZFN cleavage at target
      site

<400> SEQUENCE: 33
ctacgtgcct tcgcatacgg agtttcgcgg tgggacactt gatagaaagg ctacggtagc    60
gtacttcta                                                                       69

```
<210> SEQ ID NO 34
<211> LENGTH: 69
<212> TYPE: DNA
<213> ORGANISM: artificial sequence
<220> FEATURE:
<223> OTHER INFORMATION: INDELS as a result of ZFN cleavage at target
      site

<400> SEQUENCE: 34
ctacgtgcct tcgcatacgg agtttcgtgg tgggacactt gatagaaagg ctacggtagc      60
gtacttcta                                                               69

<210> SEQ ID NO 35
<211> LENGTH: 69
<212> TYPE: DNA
<213> ORGANISM: artificial sequence
<220> FEATURE:
<223> OTHER INFORMATION: INDELS as a result of ZFN cleavage at target
      site

<400> SEQUENCE: 35
ctacgtgcct tcgcatacgg agtattcgcg gtgggacact tgatagaaag gctacggtag      60
cgtacttca                                                               69

<210> SEQ ID NO 36
<211> LENGTH: 69
<212> TYPE: DNA
<213> ORGANISM: artificial sequence
<220> FEATURE:
<223> OTHER INFORMATION: INDELS as a result of ZFN cleavage at target
      site

<400> SEQUENCE: 36
tacgtgcctt cgcatacgga gtaggcgcgg tgggacactt gatagaaagg ctacggtagc      60
gtacttcta                                                               69

<210> SEQ ID NO 37
<211> LENGTH: 69
<212> TYPE: DNA
<213> ORGANISM: artificial sequence
<220> FEATURE:
<223> OTHER INFORMATION: INDELS as a result of ZFN cleavage at target
      site

<400> SEQUENCE: 37
tacgtgcctt cgcatacgga gtattcgcgg tgggacactt gatagaaagg ctacggtagc      60
gtacttcta                                                               69

<210> SEQ ID NO 38
<211> LENGTH: 69
<212> TYPE: DNA
<213> ORGANISM: artificial sequence
<220> FEATURE:
<223> OTHER INFORMATION: INDELS as a result of ZFN cleavage at target
      site

<400> SEQUENCE: 38
tacgtgcctt cgcatacgga gtcattcgcg gtgggacact tgatagaaag gctacggtag      60
cgtacttct                                                               69

<210> SEQ ID NO 39
<211> LENGTH: 68
<212> TYPE: DNA
```

-continued

<213> ORGANISM: artificial sequence
<220> FEATURE:
<223> OTHER INFORMATION: INDELS as a result of ZFN cleavage at target
     site

<400> SEQUENCE: 39
tacgtgcctt cgcatacgga gtttcgcggt gggacacttg atagaaaggc tacggtagcg      60
tacttcta                                                              68

<210> SEQ ID NO 40
<211> LENGTH: 69
<212> TYPE: DNA
<213> ORGANISM: artificial sequence
<220> FEATURE:
<223> OTHER INFORMATION: INDELS as a result of ZFN cleavage at target
     site

<400> SEQUENCE: 40
tacgtgcctt cgcatacgga gtcattcgcg gtgggacact tgatagaaag gctacggtag      60
cgtactcta                                                             69

<210> SEQ ID NO 41
<211> LENGTH: 69
<212> TYPE: DNA
<213> ORGANISM: artificial sequence
<220> FEATURE:
<223> OTHER INFORMATION: INDELS as a result of ZFN cleavage at target
     site

<400> SEQUENCE: 41
acgtgccttc gcatacggag tcattcgcgg tgggacactt gatagaaagg ctacggtagc      60
gtacttcta                                                             69

<210> SEQ ID NO 42
<211> LENGTH: 68
<212> TYPE: DNA
<213> ORGANISM: artificial sequence
<220> FEATURE:
<223> OTHER INFORMATION: INDELS as a result of ZFN cleavage at target
     site

<400> SEQUENCE: 42
acgtgccttc gcatacggag taggcgcggt gggacacttg atagaaaggc tacggtagcg      60
tacttcta                                                              68

<210> SEQ ID NO 43
<211> LENGTH: 68
<212> TYPE: DNA
<213> ORGANISM: artificial sequence
<220> FEATURE:
<223> OTHER INFORMATION: INDELS as a result of ZFN cleavage at target
     site

<400> SEQUENCE: 43
acgtgccttc gcatacggag tattcgcggt gggacacttg atagaaaggc tacggtagcg      60
tacttcta                                                              68

<210> SEQ ID NO 44
<211> LENGTH: 69
<212> TYPE: DNA
<213> ORGANISM: artificial sequence
<220> FEATURE:
<223> OTHER INFORMATION: INDELS as a result of ZFN cleavage at target
     site -continued

```
<400> SEQUENCE: 44
cgtgccttcg catacggagt agtttcgcgg tgggacactt gatagaaagg ctacggtagc      60
gtacttcta                                                            69

<210> SEQ ID NO 45
<211> LENGTH: 67
<212> TYPE: DNA
<213> ORGANISM: artificial sequence
<220> FEATURE:
<223> OTHER INFORMATION: INDELS as a result of ZFN cleavage at target
      site

<400> SEQUENCE: 45
cgtgccttcg catacggagt aggcgcggtg ggacacttga tagaaaggct acggtagcgt      60
acttcta                                                              67
```

HAPLOID MAIZE TRANSFORMATION

CROSS-REFERENCE TO RELATED APPLICATIONS

This application claims the benefit of U.S. Provisional Application No. 61/985,042 filed on Apr. 28, 2014, which is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing file named "75428_US_PSP_SEQ_LISTING_ST25.Txt" created on Apr. 17, 2014, having a size of 10,046 bytes that is filed concurrently with the specification. The sequence listing contained in this ASCII formatted document is part of the specification and is herein incorporated by reference in its entirety.

FIELD OF THE INVENTION

The disclosure relates generally to plants, plant tissues and cell lines, regenerating plants, and methods for introducing and/or rearranging nucleic acid therein. Methods are provided for transformation, including the site-specific insertion, of exogenous DNA and gene editing in maize androgenic-derived haploid cells.

BACKGROUND

Transgenic maize production typically involves the delivery of a transgene via *Agrobacterium* co-cultivation or microparticle bombardment into diploid somatic tissues such as the scutellar region of the immature zygotic embryo. These procedures typically lead to integrated transgenes that are 'hemizygous' in primary transformants ($T_0$) and segregate in the $T_1$ plant generation. Moving the transgene into other genetic backgrounds requires introgression via backcrossing. Accordingly, such methods for delivering transgenes into the genome of diploid somatic tissues or cells and moving the transgenes into other genetic backgrounds can be laborious, resource intensive, and time-consuming.

The site-specific delivery of transgenes to one or more predetermined locations in the genome (genome editing) of diploid plants using polynucleotides encoding site-specific nucleases can present an additional set of challenges due to the fact that the diploid genome has two corresponding sets of homologous chromosomes and these encoded site-specific nucleases modify target sites by cleavage of either one or both chromosomes of a homologous pair. Mutations resulting from imperfect repair of cleaved sites are not uncommon. Furthermore, because the genomic repair process is template-based, the repair process can use either the incoming donor polynucleotide or allelic sequence on the corresponding homologous chromosome as a template. Thus, in diploid cells, allelic sequences on the corresponding homologous chromosome can compete with the incoming donor polynucleotide. When this process results in the undesirable repair of the cleaved chromosome based on the corresponding homologous chromosome (instead of the donor polynucleotide), the efficiency of targeted transgene integration is thereby reduced.

Several plant transformation methods have been described that result in the random integration of a transgene into the haploid genome of maize. These methods include the random integration of transgenes via polyethylene glycol treatment of haploid protoplasts (Sukhapinda et al., 1993, *Plant Cell Reports,* 13:63-68; Jardinaud et al., 1995) microparticle bombardment of microspore-derived embryo-like structures *Protoplasma,* 187:138-143) and *Agrobacterium* co-cultivation of maternally-derived embryos (U.S. Pat. No. 7,572,635). However, the stable, site-specific (targeted) modification of selected locations in the haploid genome of maize remains unexplored.

Therefore, there is a desire for a method of making stable and targeted modifications of the haploid genome in maize.

Furthermore, in a haploid cell there is only a single set of chromosomes, i.e., no corresponding allelic sequence for each given gene, the incoming donor polynucleotide is a readily-available template for homology-directed repair without interference from the corresponding homologous chromosome serving as a repair template and mutations are readily revealed. The phenotypes of many mutations, e.g., knockouts, are recessive such that they are not observed in diploid tissue but can be seen in haploids. Thus, there remains a need for compositions and methods for the transformation and mutagenesis via site-specific nucleases within androgenic derived, haploid cell lines and the subsequent cleavage of haploid genomic DNA, and, optionally, the targeted integration of a donor polynucleotide or the targeted modification of a specific sequence, e.g., mutation, within androgenic-derived, haploid cell line, e.g., haploid genome of microspore-derived plant tissue cultures.

Accordingly, the present disclosure provides novel compositions and methods for the transformation and delivery of site-specific nucleases within androgenic-derived, haploid cell line, e.g., haploid genome of microspore-derived plant tissue cultures. The application of the microspore-derived plant tissue culture transformation method can result in increased efficiency of site-specific nuclease integration within the plant genome, thereby reducing the requirement for screening for large number of transformation events and subsequently reducing the costs and personnel time associated with completion of these types of experiments. For example, deployment of the transformation of haploid genome of microspore-derived plant can be used to integrate a donor DNA within a specific genomic site and to obtain homozygous plants without the requirements of expensive and laborious screening of tens of thousands of plant events. In addition, the use of androgenic, haploid cell lines for site-specific nucleases-mediated targeted mutagenesis allows for the efficient identification and isolation of recessive mutations.

BRIEF SUMMARY

The present disclosure is based, in part, on the unexpected discovery of a method for the stable and targeted modification of the haploid genome by site-specific mutagenesis or donor transgene integration in maize haploid tissue or cells. The disclosed method of genomic modification can be used with a method for chromosome doubling to make the site-specific mutations or transgenes instantaneously homozygous in a completely fixed genetic background. Furthermore, the disclosed method of stable genomic modification in haploid tissue or cells may be more efficient than other methods in diploid tissue. In diploid tissue, each genomic sequence on a first chromosome has a corresponding allelic sequence on a second chromosome which serves as the template in a homology-directed repair that has evolved to repair any mutations or transgenes inserted in the first chromosome. By contrast, haploid tissues or cells are missing the second corresponding chromosome, i.e., they lack the repair template used by homology-directed repair to remove newly introduced mutations or transgenes. In some cases, the incoming donor polynucleotide may be the most readily-available template for homology-directed repair, thus, helping to ensure that a desired targeted modification is stably integrated into the haploid genome. Additionally, the disclosed method is also useful for revealing stable genomic modification mutations, e.g., knockouts and gene inactivations, which have recessive phenotypes. In diploid tissues, recessive phenotypes are not apparent, whereas, such targeted genomic modifications leading to recessive phenotypes may be observed in haploid tissues.

In one aspect, the subject disclosure relates to a method for modifying a maize genome, the method comprising providing maize microspore-derived, transformation-competent haploid tissue comprising a haploid tissue genome; delivering a polynucleotide encoding a site-specific nuclease to the transformation-competent haploid tissue; and, confirming that the haploid tissue genome is modified by the encoded site-specific nuclease. In some embodiments, the transformation-competent haploid tissue is embryo or callus tissue. In the disclosed methods, the polynucleotide encoding the site-specific nuclease polynucleotide is delivered to the transformation-competent haploid tissue via a plant transformation method. In certain embodiments, the plant transformation method includes any method of the group consisting of a microparticle bombardment transformation method, *Agrobacterium* transformation method, calcium phosphate transformation method, polybrene transformation method, electroporation transformation method, ultrasonic transformation method, liposome transformation method, microinjection transformation method, naked DNA transformation method, plasmid vector transformation method, viral vector transformation method, silicon carbide mediated transformation method, aerosol beaming transformation method, and PEG transformation method. In any of the disclosed methods, the site-specific nuclease polynucleotide encodes a nuclease selected including a Zinc Finger Nuclease, TALEN nuclease, meganuclease, and CRISPR nuclease. In some embodiments, the site-specific nuclease preferentially cut a genomic DNA target region of the haploid maize genome. In particular embodiments, two strands of the genomic DNA are cut. In another embodiment, a single strand of the genomic DNA is cut. In additional embodiments, any of the foregoing methods can further include delivering a donor polynucleotide, and stably integrating the donor polynucleotide in the modified haploid tissue genome. In some embodiments, each donor polynucleotide comprises at least one domain that is at least 85% identical to the genomic DNA target region of the haploid tissue genome. In further embodiments, the donor polynucleotide comprises two domains that are at least 85% identical to two different sequences in the genomic DNA target region of the haploid tissue genome. In additional embodiments of any of the methods disclosed herein for modifying a haploid maize genome, the microspore derived, transformation competent tissue is from maize having elite performance characteristics. For example, the microspore derived, transformation competent tissue can be from hybrid maize derived from crossing an elite maize line with a different maize line having high microspore culture response. Additionally in any of the disclosed methods, confirming that the haploid tissue genome is modified comprises performing a PCR based assay, Southern blot assay, Northern blot assay, protein expression assay, Western blot assay, ELISA assay, or Next Generation Sequencing assay.

The transformation-competent haploid tissue derived from a maize microspore of any of the disclosed methods can be obtained by: harvesting microspore-containing tassels from maize; incubating the tassels at a temperature of about 4-12° C.; isolating microspore-containing anther from the tassels; culturing anthers in anther culture medium to generate microspore-derived embryos; and, culturing the microspore-derived embryos in callus medium to thereby generate the microspore-derived, transformation-competent haploid tissue.

In another embodiment, the haploid tissue comprising the modified haploid tissue genome can be further treated with a chromosome doubling agent, thereby producing dihaploid maize tissue comprising a modified dihaploid maize genome. The dihaploid maize tissue can be cultured or regenerated into a dihaploid maize plant comprising the modified dihaploid maize genome. In addition, such dihaploid maize plant is homozygous for the genomic modification of the haploid tissue.

In yet another aspect, the subject disclosure relates to a method for targeted integration of a donor, the method comprising: providing a maize microspore-derived, transformation-competent haploid tissue comprising haploid tissue genome; delivering one or more donor polynucleotides and one or more polynucleotides encoding site-specific nucleases to the transformation-competent haploid tissue; and, confirming that the one or more donor polynucleotides are integrated into the haploid tissue genome and the haploid tissue genome is thereby modified. In some embodiments, the transformation-competent haploid tissue is embryo or callus tissue. In these methods, delivering the one or more donor polynucleotides and the one or more polynucleotides encoding site-specific nucleases to the transformation-competent haploid tissue can be done via a plant transformation method. In some embodiments, the plant transformation method includes a microparticle bombardment transformation method, *Agrobacterium* transformation method, calcium phosphate transformation method, polybrene transformation method, electroporation transformation method, ultrasonic transformation method, liposome transformation method, microinjection transformation method, naked DNA transformation method, plasmid vector transformation method, viral vector transformation method, silicon carbide mediated transformation method, aerosol beaming transformation method, and PEG transformation method. In additional embodiments, the site-specific nuclease polynucleotide encodes a nuclease selected from the group consisting of a Zinc Finger Nuclease, TALEN nuclease, meganuclease, and CRISPR nuclease. In some embodiments, the one or more polynucleotides encoding site-specific nucleases that preferentially cut a genomic DNA target region of the haploid tissue genome. In further embodiments, any of the disclosed methods herein further include a stable integration of the one or more donor polynucleotides within the haploid tissue genome. For example, the one or more donor polynucleotides can integrate within the target region via homology directed repair or via non homologous end joining repair. In any of the methods disclosed herein for modifying a haploid maize genome, the microspore derived, transformation competent tissue is from maize having elite performance characteristics. For example, the microspore derived, transformation competent tissue is from hybrid maize derived from crossing an elite maize line with a different maize line having high microspore culture response. In any of the methods disclosed herein for modifying a haploid maize genome, the haploid tissue genome includes confirming the integration into the haploid tissue genome comprises performing a PCR based assay, Southern blot assay, Northern blot assay, protein expression assay, Western blot assay, ELISA assay, or Next Generation Sequencing assay. In any of the disclosed embodiments, the one or more donor polynucleotides into the haploid tissue genome can impart (e.g., encodes a gene that, when expressed, provides maize having) an agronomic trait. For example, the agronomic trait can be selected from an insecticidal resistance trait, herbicide tolerance trait, nitrogen use efficiency trait, water use efficiency trait, nutritional quality trait, DNA binding trait, and selectable marker trait. In any of the disclosed embodiments, the donor polynucleotide can be stably expressed within the maize plant. Furthermore, any of the disclosed methods whereby integrating a donor polynucleotide into the haploid tissue genome can further include treating the haploid tissue with a chromosome doubling agent to produce a doubled haploid tissue that comprises and is homozygous for the integrated donor polynucleotide.

In another aspect, the subject disclosure relates to a plant comprising the donor polynucleotide. In an embodiment, the plant comprises a haploid genome. In a further embodiment, the plant comprises a dihaploid genome. Such plants can be regenerated from the tissue comprising the modified haploid tissue genome or modified dihaploid tissue genome of any of the methods disclosed herein.

In another aspect, the subject disclosure relates to a method for introducing a mutation within a haploid genome of maize, the method comprising: providing maize microspore-derived, transformation-competent haploid tissue comprising a haploid tissue genome; delivering a polynucleotide encoding a site-specific nuclease to the transformation-competent haploid tissue; and, confirming that the haploid maize genome comprises a mutation introduced by the encoded site-specific nuclease polynucleotides. The transformation-competent haploid tissue can be an embryo or callus tissue. The one or more polynucleotides encoding site-specific nucleases can be delivered to the transformation-competent haploid tissue via a plant transformation method. The plant transformation method can be selected from a microparticle bombardment transformation method, *Agrobacterium* transformation method, calcium phosphate transformation method, polybrene transformation method, electroporation transformation method, ultrasonic transformation method, liposome transformation method, microinjection transformation method, naked DNA transformation method, plasmid vector transformation method, viral vector transformation method, silicon carbide mediated transformation method, aerosol beaming transformation method, and PEG transformation method. In any of the disclosed methods, the site-specific nuclease polynucleotide encodes a nuclease including a Zinc Finger Nuclease, TALEN nuclease, meganuclease, and CRISPR nuclease. The encoded site-specific nuclease polynucleotide can be one that preferentially cuts genomic DNA at a target region of the haploid maize genome. In any of the disclosed methods, the microspore derived, transformation competent tissue can be from maize having elite performance characteristics. For example, the microspore derived, transformation competent tissue can be from hybrid maize derived from crossing an elite maize line with a different maize line having high microspore culture response. In any of the disclosed methods, confirming that the one or more polynucleotides encoding site-specific nucleases introduce a mutation into the genome can be done by a PCR based assay, Southern blot assay, Northern blot assay, protein expression assay, Western blot assay, ELISA assay, and Next Generation Sequencing assay. In any of the disclosed methods, confirming that the haploid maize genome is modified comprises performing a PCR based assay, Southern blot assay, Northern blot assay, protein expression assay, Western blot assay, ELISA assay, and Next Generation Sequencing assay. The mutation introduced according to the disclosed method can down-regulate expression of an endogenous gene. In some embodiments, the down-regulation of an endogenous gene results in an altered metabolic pathway. Furthermore, any of the disclosed methods whereby integrating a donor polynucleotide into the haploid tissue genome can further include treating the haploid tissue with a chromosome doubling agent to produce a doubled haploid tissue that comprises and is homozygous for the integrated donor polynucleotide.

In an aspect, the subject disclosure relates to a plant comprising the introduced mutation. In some embodiments, the plant comprises a haploid tissue genome. In other embodiments, the plant comprises a dihaploid tissue genome. Such plants can be regenerated from modified haploid tissue or dihaploid tissue produced according to any of the methods disclosed herein.

In an aspect, the subject disclosure relates to a method for introducing one or more polynucleotides encoding site-specific nucleases into an androgenic-derived, haploid cell line. In some embodiments, the method comprises: providing a transformation-competent androgenic derived, haploid cell line; delivering the one or more polynucleotides encoding a site-specific nuclease to the transformation-competent androgenic-derived, haploid cell line; and, confirming that the one or more polynucleotides encoding a site-specific nuclease modify the genome of the androgenic-derived, haploid cell line. In one embodiment, the androgenic-derived, haploid cell line is a haploid microspore cell line. In another embodiment, the haploid microspore cell line is propagated into an embryo or callus tissue. In a further embodiment, the method comprises delivering the one or more polynucleotides encoding site-specific nucleases to the androgenic derived, haploid cell line via a plant transformation method. The polynucleotides can be delivered via a plant transformation method such as, for example, a biolistics transformation method, *Agrobacterium* transformation method, calcium phosphate transformation method, polybrene transformation method, electroporation transformation method, ultrasonic transformation method, liposome transformation method, microinjection transformation method, naked DNA transformation method, plasmid vector transformation method, viral vector transformation method, silicon carbide mediated transformation method, aerosol beaming transformation method, and PEG transformation method. Each of the site specific nuclease polynucleotides can encodes a nuclease selected from a Zinc Finger Nuclease, TALEN nuclease, meganuclease, and CRISPR nuclease. In yet another embodiment, the method comprises delivering the one or more polynucleotides encoding a site-specific nuclease that preferentially modify a genomic DNA target region of the genome. In particular embodiments, a single strand two strands of the genomic DNA target region are cut. In other embodiment, a single strand of the genomic DNA target region is cut. In any of the disclosed methods that include delivering one or more donor polynucleotides, the one or more donor polynucleotides can be stably integrated within the modified genome. In certain embodiments, each donor polynucleotide comprises at least one domain that is at least 85% identical to the genomic DNA target region of the genome. In further embodiments, each donor polynucleotide comprises two domains that are at least 85% identical to two different sequences in the genomic DNA target region of the genome. The donor polynucleotide can integrate within the genomic DNA target region via homology directed repair or via non homologous end joining repair. In another embodiment, confirming that the polynucleotide encoding the site-specific nuclease modifies the genome is performed by a PCR based assay, Southern blot assay, Northern blot assay, protein expression assay, Western blot assay, ELISA assay, or Next Generation Sequencing assay. In another embodiment, confirming that the one or more donor polynucleotides is integrated into the genomic DNA target region comprises performing a PCR based assay, Southern blot assay, Northern blot assay, protein expression assay, Western blot assay, ELISA assay, and Next Generation Sequencing assay.

In yet further embodiments, any of the disclosed methods can further comprise obtaining haploid tissue comprising the modified the genome of the androgenic-derived, haploid cell line; treating the haploid tissue with a chromosome doubling agent; producing dihaploid tissue comprising a modified dihaploid genome; and, culturing the dihaploid tissue into a dihaploid plant comprising the modified dihaploid genome. In an additional embodiment, the androgenic-derived, haploid cell line is obtained from a maize plant. In any of the disclosed embodiments, the modified dihaploid genome results from a cleavage of the genome.

BRIEF DESCRIPTION OF THE FIGURES

FIG. 4 provides an illustration of sequence alignments showing insertions and deletions at the PPL1 cleavage site demonstrating targeted mutagenesis following bombardment of haploid callus. Sequences are provided in the alignment to exemplify the deletions and insertions as SEQ ID NO:33 to SEQ ID NO:45. These altered sequences are compared to SEQ ID NO:32 which provides the genomic DNA target sequence that Zinc Finger Nucleases were designed to bind and cleave.

FIG. 5 provides a histogram of nuclei from diploidized callus following colchicine treatment demonstrating effective chromosome doubling.

DETAILED DESCRIPTION

Figure 1:
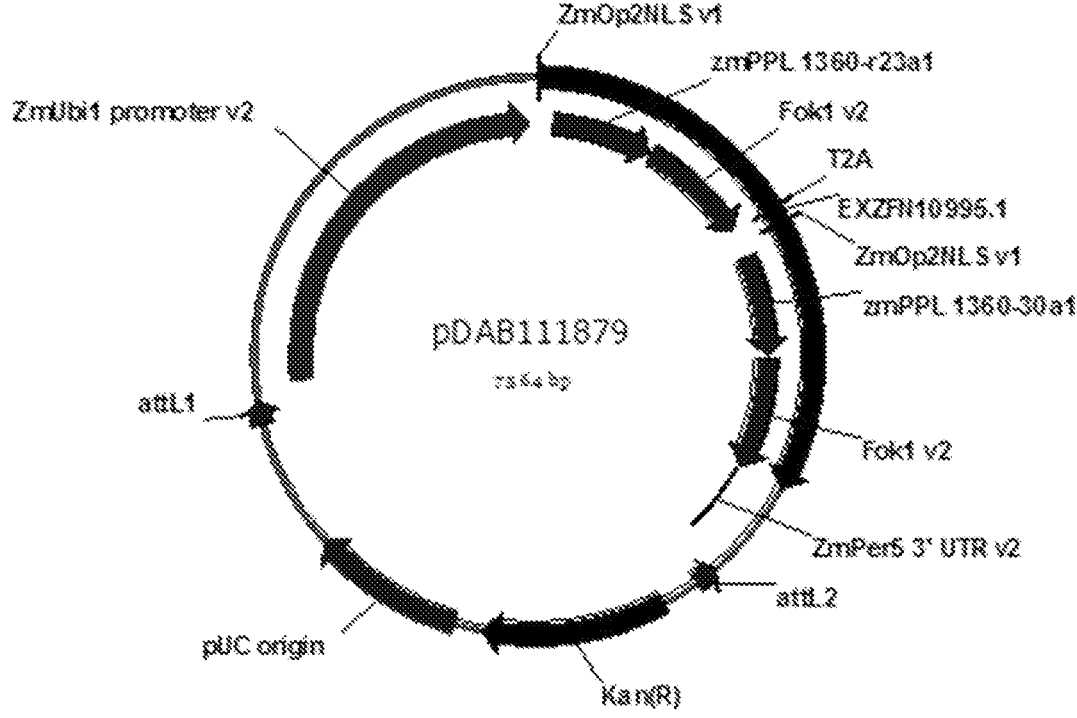
FIG. 1 provides a plasmid map of pDAB111879. This plasmid map is of a ZFN construct for targeted genome modification.

The present disclosure provides a method for modifying a maize genome in transformation-competent haploid tissue derived from a maize microspore. The method includes delivering one or more polynucleotides encoding site-specific nucleases to the transformation-competent haploid tissue, and confirming that the one or more encoded site-specific nucleases modify the haploid maize genome.

Androgenic-derived cell lines can be maintained as a microspore-derived plant tissue culture. The microspore-derived plant tissue culture results in a haploid tissue culture that contains only one set of chromosomes. The androgenic-derived, haploid cell lines are generated from androgenic tissues such as microspores and pollen, or sporophytic tissues (e.g., paternal haploid embryos), and can be maintained as an embryo or callus, suspension or protoplast culture. In maize, reports of androgenesis and haploid plant production date back to the 1970s (Ku et al., 1978, *Proc. Symp. Plant Tissue Cult.* 35-42), however, the low production frequencies of androgenic embryos as well as the difficulties associated with plant regeneration and chromosome doubling preclude the general use of anther or microspore-derived plant culture in applied breeding. Many of these fundamental problems were overcome with the development of highly responsive germplasm (Petolino et al., 1988, *Theor. Appl. Genet.* 76:157-159) and in vitro techniques for chromosome doubling (Wan et al., 1991, *Theor. Appl. Genet.* 77:889-892), although in maize, for the most part, this technique has been largely abandoned.

The disclosure also provides a method for targeted integration of a donor polynucleotide into a haploid maize genome in transformation-competent haploid tissue derived from a maize microspore. The method includes delivering one or more donor polynucleotides and one or more polynucleotides encoding site-specific nucleases to the transformation-competent haploid tissue; and, confirming that the one or more of the donor polynucleotides are integrated into the haploid genome of maize.

The disclosure further provides a method for introducing a mutation within a haploid maize genome in transformation-competent haploid tissue derived from a maize microspore; delivering polynucleotides encoding one or more site-specific nucleases to the transformation-competent haploid tissue; and, confirming that the one or more encoded site-specific nuclease modify the haploid maize genome, wherein the haploid maize genome is mutated by the cleavage as indicated by the presence of insertions or deletions within the genomic DNA.

In another aspect, the disclosure provides a method for modifying the genome of transformation-competent androgenic-derived, haploid cell line. The method includes delivering the one or more polynucleotides encoding site-specific nucleases to the transformation-competent androgenic-derived, haploid cell line, and confirming that the encoded site-specific nucleases modify the genome of the androgenic-derived, haploid cell line, wherein the genome of the androgenic-derived, haploid cell line is modified by the cleavage.

Definitions

Unless defined otherwise, all technical and scientific terms used herein have the same meaning as commonly understood by one of ordinary skill in the art to which this disclosure relates. In case of conflict, the present application including the definitions will control. Unless otherwise required by context, singular terms shall include pluralities and plural terms shall include the singular. All publications, patents and other references mentioned herein are incorporated by reference in their entireties for all purposes as if each individual publication or patent application were specifically and individually indicated to be incorporated by reference, unless only specific sections of patents or patent publications are indicated to be incorporated by reference.

In order to further clarify this disclosure, the following terms, abbreviations and definitions are provided.

As used herein, the terms "comprises," "comprising," "includes," "including," "has," "having," "contains," or "containing," or any other variation thereof, are intended to be non-exclusive or open-ended. For example, a composition, a mixture, a process, a method, an article, or an apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of an embodiment of the disclosure are intended to be nonrestrictive regarding the number of instances, i.e., occurrences of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as disclosed in the application.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, and includes protoplast cells without a cell wall and plant cells with a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "isolated" refers to a biological component (including a nucleic acid or protein) that has been separated, produced apart from other biological components in the cell of the organism in which the component naturally occurs (i.e., other chromosomal and extra-chromosomal DNA and RNA, and proteins).

As used herein, the term "purified" in reference to nucleic acid molecules does not require absolute purity (such as a homogeneous preparation); instead, it represents an indication that the sequence is relatively more pure than in its native cellular environment (compared to the natural level this level should be at least 2-5 fold greater, e.g., in terms of concentration or gene expression levels). The claimed DNA molecules obtained directly from total DNA or from total RNA. In addition, cDNA clones are not naturally occurring, but rather are preferably obtained via manipulation of a partially purified, naturally occurring substance (messenger RNA). The construction of a cDNA library from mRNA involves the creation of a library. Individual cDNA clones can be produced from the library by clonal selection of the cells carrying the cDNA library. Thus, the process which includes the construction of a cDNA library from mRNA and selection of distinct cDNA clones yields an approximately $10^6$-fold purification of the native message. Likewise, a promoter or gene DNA sequence could be cloned into a plasmid. Such a clone is not naturally occurring, but rather is preferably obtained via manipulation of a partially purified, naturally occurring substance such as a genomic DNA library. Thus, purification of at least one order of magnitude, preferably two or three orders, and more preferably four or five orders of magnitude is favored in these techniques.

Similarly, synthetic represents an indication that a chemical or functional change in the component DNA sequence has occurred. Nucleic acid molecules and proteins that have been "synthesized" include nucleic acid molecules and proteins generated by PCR amplification or by recombinant methods, wherein a purified polynucleotide is further modified by the incorporation within a plasmid or vector. The term "synthetic" also embraces nucleic acids and proteins prepared by recombinant DNA methods in a host cell (e.g., plant cells), as well as chemically-synthesized nucleic acid molecules, proteins, and peptides.

In engineering a gene for expression in plants, the codon bias of the prospective host plant(s) may be determined, for example, through use of publicly available DNA sequence databases to find information about the codon distribution of plant genomes or the protein coding regions of various plant genes. Once an optimized (e.g., a plant-optimized) DNA sequence has been designed on paper, or in silico, actual DNA molecules may be synthesized in the laboratory to correspond in sequence precisely to the designed sequence. Such synthetic nucleic acid molecule molecules can be cloned and otherwise manipulated exactly as if they were derived from natural or native sources.

As used herein, the terms "polynucleotide," "nucleic acid," and "nucleic acid molecule" are used interchangeably, and may encompass a singular nucleic acid; plural nucleic acids; a nucleic acid fragment, variant, or derivative thereof; and nucleic acid construct (e.g., messenger RNA (mRNA) and plasmid DNA (pDNA)). A polynucleotide or nucleic acid may contain the nucleotide sequence of a full-length cDNA sequence, or a fragment thereof, including untranslated 5' and/or 3' sequences and coding sequence(s). A polynucleotide or nucleic acid may be comprised of any polyribonucleotide or polydeoxyribonucleotide, which may include unmodified ribonucleotides or deoxyribonucleotides or modified ribonucleotides or deoxyribonucleotides. For example, a polynucleotide or nucleic acid may be comprised of single- and double-stranded DNA; DNA that is a mixture of single- and double-stranded regions; single- and double-stranded RNA; and RNA that is mixture of single- and double-stranded regions. Hybrid molecules comprising DNA and RNA may be single-stranded, double-stranded, or a mixture of single- and double-stranded regions. The foregoing terms also include chemically, enzymatically, and metabolically modified forms of a polynucleotide or nucleic acid.

It is understood that a specific DNA refers also to the complement thereof, the sequence of which is determined according to the rules of deoxyribonucleotide base-pairing.

As used herein, the term "gene" refers to a nucleic acid that encodes a functional product (RNA or polypeptide/protein). A gene may include regulatory sequences preceding (5' non-coding sequences) and/or following (3' non-coding sequences) the sequence encoding the functional product.

As used herein, the term "coding sequence" refers to a nucleic acid sequence that encodes a specific amino acid sequence. A "regulatory sequence" refers to a nucleotide sequence located upstream (e.g., 5' non-coding sequences), within, or downstream (e.g., 3' non-coding sequences) of a coding sequence, which influence the transcription, RNA processing or stability, or translation of the associated coding sequence. Regulatory sequences include, for example and without limitation: promoters; translation leader sequences; introns; polyadenylation recognition sequences; RNA processing sites; effector binding sites; and stem-loop structures.

As used herein, the term "polypeptide" includes a singular polypeptide, plural polypeptides, and fragments thereof. This term refers to a molecule comprised of monomers (amino acids) linearly linked by amide bonds (also known as peptide bonds). The term "polypeptide" refers to any chain or chains of two or more amino acids, and does not refer to a specific length or size of the product. Accordingly, peptides, dipeptides, tripeptides, oligopeptides, protein, amino acid chain, and any other term used to refer to a chain or chains of two or more amino acids, are included within the definition of "polypeptide," and the foregoing terms are used interchangeably with "polypeptide" herein. A polypeptide may be purified from a natural biological source or produced by recombinant technology, but a specific polypeptide is not necessarily translated from a specific nucleic acid. A polypeptide may be generated in any appropriate manner, including for example and without limitation, by chemical synthesis.

As used herein, the term "native" refers to the form of a polynucleotide, gene or polypeptide that is found in nature with its own regulatory sequences, if present. The term "endogenous" refers to the native form of the polynucleotide, gene or polypeptide in its natural location in the organism or in the genome of the organism.

In contrast, the term "heterologous" refers to a polynucleotide, gene or polypeptide that is not normally found at its location in the reference (host) organism. For example, a heterologous nucleic acid may be a nucleic acid that is normally found in the reference organism at a different genomic location. By way of further example, a heterologous nucleic acid may be a nucleic acid that is not normally found in the reference organism. A host organism comprising a heterologous polynucleotide, gene or polypeptide may be produced by introducing the heterologous polynucleotide, gene or polypeptide into the host organism. In particular examples, a heterologous polynucleotide comprises a native coding sequence, or portion thereof, that is reintroduced into a source organism in a form that is different from the corresponding native polynucleotide. In particular examples, a heterologous gene comprises a native coding sequence, or portion thereof, that is reintroduced into a source organism in a form that is different from the corresponding native gene. For example, a heterologous gene may include a native coding sequence that is a portion of a chimeric gene including non-native regulatory regions that is reintroduced into the native host. In particular examples, a heterologous polypeptide is a native polypeptide that is reintroduced into a source organism in a form that is different from the corresponding native polypeptide.

A heterologous gene or polypeptide may be a gene or polypeptide that comprises a functional polypeptide or nucleic acid sequence encoding a functional polypeptide that is fused to another genes or polypeptide to produce a chimeric or fusion polypeptide, or a gene encoding the same. Genes and proteins of particular embodiments include specifically exemplified full-length sequences and portions, segments, fragments (including contiguous fragments and internal and/or terminal deletions compared to the full-length molecules), variants, mutants, chimerics, and fusions of these sequences.

"Endogenous" refers to materials originating from within the organism or cell.

"Exogenous" refers to materials originating from outside of the organism or cell. As used herein, exogenous is intended to refer to any nucleic acid from a source other than the recipient cell or tissue, regardless of whether a similar (but not identical) nucleic acid may already be present in the recipient cell or tissue.

As used herein, the term "modification" may refer to a change in a particular reference polynucleotide that results in reduced, substantially eliminated, or eliminated activity of a polypeptide encoded by the reference polynucleotide. Alternatively, the term "modification" may refer to a change in a reference polynucleotide that results in increased or enhanced activity of a polypeptide encoded by the reference polynucleotide, as well as a change in a reference polypeptide that results in increased or enhanced activity of the reference polypeptide. When used to describe the activity of a site-specific nuclease, modification can mean cleaving a portion of the reference molecule (e.g., a cleavage of genomic DNA; either a double strand or single strand cleavage of the genomic DNA). Changes such as the foregoing may result in, for example and without limitation: deleting a portion of the reference molecule; mutating the reference molecule (e.g., via spontaneous mutagenesis, via random mutagenesis, via mutagenesis caused by mutator genes, and via transposon mutagenesis); substituting a portion of the reference molecule; inserting an element into the reference molecule; down-regulating expression of the reference molecule; altering the cellular location of the reference molecule; altering the state of the reference molecule (e.g., via methylation of a reference polynucleotide, and via phosphorylation or ubiquitination of a reference polypeptide); removing a cofactor of the reference molecule; introduction of an antisense RNA/DNA targeting the reference molecule; introduction of an interfering RNA/DNA targeting the reference molecule; chemical modification of the reference molecule; covalent modification of the reference molecule; irradiation of the reference molecule with UV radiation or X-rays; homologous recombination that alters the reference molecule; mitotic recombination that alters the reference molecule; replacement of the promoter of the reference molecule; and/or combinations of any of the foregoing.

Guidance in determining which nucleotides or amino acid residues may be modified in a specific example may be found by comparing the sequence of the reference polynucleotide or polypeptide with that of homologous (e.g., homologous yeast or bacterial) polynucleotides or polypeptides, and maximizing the number of modifications made in regions of high homology (conserved regions) or consensus sequences.

The term "promoter" refers to a DNA sequence capable of controlling the expression of a nucleic acid coding sequence or functional RNA. In examples, the controlled coding sequence is located 3' to a promoter sequence. A promoter may be derived in its entirety from a native gene, a promoter may be comprised of different elements derived from different promoters found in nature, or a promoter may even comprise synthetic DNA segments. It is understood by those skilled in the art that different promoters can direct the expression of a gene in different tissues or cell types, or at different stages of development, or in response to different environmental or physiological conditions. Examples of all of the foregoing promoters are known and used in the art to control the expression of heterologous nucleic acids. Promoters that direct the expression of a gene in most cell types at most times are commonly referred to as "constitutive promoters." Furthermore, while those in the art have (in many cases unsuccessfully) attempted to delineate the exact boundaries of regulatory sequences, it has come to be understood that DNA fragments of different lengths may have identical promoter activity. The promoter activity of a particular nucleic acid may be assayed using techniques familiar to those in the art.

The term "operably linked" refers to an association of nucleic acid sequences on a single nucleic acid, wherein the function of one of the nucleic acid sequences is affected by another. For example, a promoter is operably linked with a coding sequence when the promoter is capable of effecting the expression of that coding sequence (e.g., the coding sequence is under the transcriptional control of the promoter). A coding sequence may be operably linked to a regulatory sequence in a sense or antisense orientation.

The term "expression" or "expressing," as used herein, may refer to the transcription and stable accumulation of sense (mRNA) or antisense RNA derived from a DNA. Expression may also refer to translation of mRNA into a polypeptide. As used herein, the term "overexpression" refers to expression that is higher than endogenous expression of the same gene or a related gene. Thus, a heterologous gene is "overexpressed" if its expression is higher than that of a comparable endogenous gene.

As used herein, the term "transformation" or "transforming" refers to the transfer and integration of a nucleic acid or fragment thereof into a host organism, resulting in genetically stable inheritance. Host organisms containing a transforming nucleic acid are referred to as "transgenic," "recombinant," or "transformed" organisms. Known methods of transformation include, for example: *Agrobacterium tumefaciens*- or *A. rhizogenes*-mediated transformation; calcium phosphate transformation; polybrene transformation; protoplast fusion; electroporation; ultrasonic methods (e.g., sonoporation); liposome transformation; microinjection; transformation with naked DNA; transformation with plasmid vectors; transformation with viral vectors; biolistic transformation (microparticle bombardment); silicon carbide WHISKERS-mediated transformation; aerosol beaming; and PEG-mediated transformation.

As used herein, the term "introduced" (in the context of introducing a nucleic acid into a cell) includes transformation of a cell, as well as crossing a plant comprising the nucleic acid with a second plant, such that the second plant contains the nucleic acid, as may be performed utilizing conventional plant breeding techniques. Such breeding techniques are known in the art. For a discussion of plant breeding techniques, see Poehlman (1995) Breeding Field Crops, 4th Edition, AVI Publication Co., Westport CT.

Backcrossing methods may be used to introduce a nucleic acid into a plant. This technique has been used for decades to introduce traits into plants. An example of a description of backcrossing (and other plant breeding methodologies) can be found in, for example, Poehlman (1995), supra; and Jensen (1988) Plant Breeding Methodology, Wiley, New York, NY. In an exemplary backcross protocol, an original plant of interest (the "recurrent parent") is crossed to a second plant (the "non-recurrent parent") that carries the nucleic acid be introduced. The resulting progeny from this cross are then crossed again to the recurrent parent, and the process is repeated until a converted plant is obtained, wherein essentially all of the desired morphological and physiological characteristics of the recurrent parent are recovered in the converted plant, in addition to the nucleic acid from the non-recurrent parent.

As used herein, the term "isogenic" refers to two individual plants (or portions thereof e.g., seeds, cells) having a substantially identical genotype (e.g., not more than 1 gene is different between the individuals).

As used herein, the term "stable integration" or "stable transformation" "genetically stable inheritance" or "stably" refers to the introduction of a nucleic acid or polynucleotide segment within the genome of an organism (generally, a heterologous nucleic acid sequence or gene) such as a plant, plant tissue, plant organelle (i.e., a plastid or chloroplast), or plant cell that did not previously contain that nucleic acid or polynucleotide segment. The resulting integration is affixed to the genome of the plant and can be transmitted into progeny plants. Preferably, transformation results in the stable integration of the nucleic acid sequence into the genome of the plant. As used herein, the term "genome" encompasses nuclear genomes, plastid genomes, and mitochondrial genomes. Comparatively, "transient transformation" refers to the introduction of a nucleic acid fragment into the nucleus, or DNA-containing organelle, of a host organism resulting in gene expression without genetically stable inheritance.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage such that the genomic DNA is modified.

The terms "plasmid" and "vector," as used herein, refer to an extra chromosomal element that may carry one or more gene(s) that are not part of the central metabolism of the cell. Plasmids and vectors typically are circular double-stranded DNA molecules. However, plasmids and vectors may be linear or circular nucleic acids, of a single- or double-stranded DNA or RNA, and may be derived from any source, in which a number of nucleotide sequences have been joined or recombined into a unique construction that is capable of introducing a promoter fragment and a coding DNA sequence along with any appropriate 3' untranslated sequence into a cell. In examples, plasmids and vectors may comprise autonomously replicating sequences, genome integrating sequences, and/or phage or nucleotide sequences.

The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

"Haploid" refers to plant cells, tissues or plants with one set (n) of chromosomes.

"Dihaploid" or "doubled haploid" or "diploid" refer to plant cells, tissues, or plants derived from a haploid. Dihaploids have two sets (2n) of chromosomes and are typically homozygous. It is possible, however, that mutations, deletions, or insertions, or other like modifications in the DNA may lead to some deviations from the absolute homozygosity that would normally be observed in the dihaploids. Similarly, one of skill in the art may intentionally modify the dihaploid DNA by making random or targeted mutations, deletions, insertions, or by shuffling the DNA or portions thereof. Such "modified dihaploids" are encompassed by the disclosure. Polyploids may also be obtained using the methods of the present disclosure, if desired. Polyploids will have three or more sets of chromosomes and should also be homozygous except for the modifications discussed above.

"Chromosome doubling agent" refers to a chemical that doubles the number of chromosomes in the cell (e.g., from haploid to diploid or diploid to tetraploid, etc). Such agents are typically antimicrotubule agents such as colchicine, pronamide, or APM (amiprophosmethyl). Nitrous oxide has also been reported to be a doubling agent (US Pat. App. 2003/0005479, incorporated by reference herein in its entirety). One of skill in the art is familiar with the compounds that can cause chromosome doubling (e.g., by blocking normal cell cycle division etc).

"Callus" refers to a dedifferentiated proliferating mass of cells or tissue.

"Type I callus" refers to callus that is morphologically compact maize callus from which whole plants can be regenerated via organogenesis, embryogenesis or a combination of the two.

"Type II callus" refers to morphologically friable, highly embryogenic maize callus (Armstrong and Green, Planta. 164:207-214. 1985).

"Mature embryo" refers to a zygotic embryo that can be obtained approximately 15 days or more after pollination and does not typically produce regenerable callus when cultured in vitro.

"Immature embryo" refers to a zygotic embryo that can be obtained approximately 15 days or less after pollination and can typically produce regenerable callus when cultured in vitro.

The term "zygotic embryo" is used to encompass seed, mature embryos extracted from seed, mature embryos, or immature embryos capable of germination.

"Embryogenic culture" or "embryogenic cell" or "embryogenic tissue" or "embryo" or "embryo-like structure" refers to cultured plant cells and tissues capable of being regenerated into a plant.

"Plant growth regulator or plant hormone" refers to compounds that affect plant growth. The plant growth regulators include, but are not limited to, auxins, cytokinins, ABA, gibberellins, ethylene, brassinosteroids, and polyamines. Auxins affect the elongation of shoots and roots at low concentration but inhibit growth at higher levels. Commonly used auxins include picloram (4-amino-3,5,6-trichloropicolinic acid), 2,4-D (2,4-dichlorophenoxyacetic acid), IAA (indole-3-acetic acid), NAA (α-naphthaleneacetic acid), and dicamba (3,6-dichloroanisic acid). Cytokinins cause cell division, cell differentiation, and shoot differentiation. Commonly used cytokinins include kinetin, BA (6-benzylaminopurine), 2-ip (2-isopentenyladenine), BAP (6-benzylaminopurine), thidiazuron (TDZ), zeatin riboside, and zeatin.

"Monocot" or "monocotyledonous" refers to plants having a single cotyledon. Examples include cereals such as maize, rice, wheat, oat, and barley.

"Phenotype" refers to a trait exhibited by an organism resulting from the expression (or lack of expression) of nucleic acids in the genome (including non-genomic DNA and RNA such as plasmids and artificial chromosomes) and/or organelles of the organism.

"Regeneration" refers to the process of growing a plant from a plant cell or tissue.

"Selectable marker" or "screenable marker" refers to a nucleic acid sequence whose expression confers a phenotype facilitating identification of cells, tissues, or plants containing the nucleic acid sequence.

"Sporophytic" refers to plants in the phase of the life cycle that is characterized by having the double chromosome number. This is in contrast to "gametophytic", which includes microspores and pollen.

Tissues Derived from Androgenic Derived, Haploid Cell Lines

Generally, the ploidy level of a genome relates to the number of chromosome sets that are present within the nucleus of the cell. The ploidy level can vary depending upon the type of cells and/or source of cells that make up the organism. The haploid number (n) is an indication that only one set of chromosomes are present within the organism. The dihaploid or diploid number (2n) is an indication that two sets of chromosomes are present within the organism. It is common for some organisms, especially plant species, to contain even greater numbers of sets of chromosomes, e.g., triploid (3n), tetraploid (4n), pentaploid (5n), and hexaploid (6n). Such examples of increased sets of chromosomes, e.g., triploid or greater, are generally known as polyploids.

Typically, the diploid (2n) multicellular stage alternates with a haploid (n) multicellular stage throughout the life cycle of an organism. The haploid (n) stage of the life cycle of an organism is regarded as the gametophytic stage, e.g., gamete producing. Comparatively, the diploid (2n) stage of the life cycle of an organism is regarded as the sporophytic stage, e.g., spore producing. During the sporophytic stage, the organism produces microspores (i.e., spores) that are haploid (n) via a process called meiosis. The resulting microspores can produce gametes, e.g., sperm nuclei that fuse with other gametes, e.g., egg nuclei, produced by megaspores to generate a diploid zygote during fertilization.

In plants the microspores are produced in male reproductive organs. The male reproductive organs are known as anthers. The anthers produce haploid microspores which mature into pollen containing sperm nuclei. The pollen represents the beginning of a short-lived male gametophytic phase of a plants life cycle during which two sperm nuclei are delivered to the embryo sac of the ovule for double fertilization and subsequent embryo and endosperm formation. Although this stage of a higher plants life cycle typically consists of only a few cell divisions, under certain experimental conditions, microspores can be induced to undergo an altered development, leading to the production of embryo-like structures without an intervening fertilization. As such, these embryo-like structures are haploid (n). This process, referred to as androgenesis, is the biological basis for the in-vitro technique known as anther or microspore culture.

In an embodiment, a transformation-competent androgenic derived, cell line is provided. In subsequent embodiments, a haploid microspore cell line is obtained from the transformation-competent androgenic derived, cell line. In a further embodiment, a transformation-competent haploid tissue is derived from a maize microspore. Anther-derived cultures provide a rapid method of inducing homozygosity in plants which are of interest for the production of breeding lines. Anther culture involves isolating immature anthers from plants and placing them onto a medium which induces the cells within the anther, which would normally be destined to become pollen grains, the microspores, to begin dividing and form a cell culture from which plants can be regenerated. For a general discussion of anther culture, see J. M. Dunwell, "Anther and Ovary Culture", In S. W. J. Bright and M. G. K. Jones, (eds.), Cereal Tissue and Cell Culture, Martinus Nijhoff Publisher, 1985, Dordrecht, pp. 1-44. The resulting cultures are haploid and contain only a single set of chromosomes from the original plants. The plants derived from these cultures are sterile unless chromosome doubling occurs, either spontaneously or by induction, to create doubled haploids which are fully fertile and completely inbred.

Numerous studies on the in-vitro culture of gametophytic cells with the aim of producing haploid plants have been reported during the last several decades. A large number of reviews, book chapters and symposia proceedings have been published as well (see generally Chu, "Haploids in Plant Improvement", In I. K. Vasil, W. R. Scowcroft, K. J. Frey (eds.), Plant Improvement and Somatic Cell Genetics, New York: Academic Press, 1982, pp. 129-158; Heberle-Bors, 1985, "In Vitro Haploid Formation of Pollen: A Critical Review", *Theor. Appl. Genet.* 71:361-374; and, Hu and Yang, "Haploids of Higher Plants in Vitro." Berlin, Heidelberg, Springer-Verlag, 1986).

Anther culture represents a method by which, theoretically, large numbers of haploid individuals can be produced directly from anthers and/or microspores in-vitro. See, Keller et al., "Haploids from gametophytic cells—recent developments and future prospects", In C. E. Green, D. A. Somers, W. P. Hackett, D. D. Biesoer (eds.), Plant Tissue and Cell Culture, Alan R Liss, New York, pp 223-241, 1986. Haploids can be regenerated from both male and female gametophytic cells through the culture of anthers, microspores, ovaries and ovules. A positive in-vitro response will lead to the development of embryos and/or callus from which plants can be regenerated. Early events during in-vitro culture have been characterized at the cytological, ultrastructural and biochemical level (Chen et al., 1984, "Segmentation Patterns and Mechanisms of Genome Multiplication in Cultured Microspores of Barley", *J. Can, Genet. Cytol.,* 26:475-483; Raghavan, 1984, "Protein Synthetic Activity during Normal Pollen Development and During Induced Pollen Embryogenesis in Hyoscyamus niger", *J. Can Bot.,* 62:2493-2513; Huang, "Ultrastructural Aspects of Pollen Embryogenesis in Hordeum, Triticum and Paeonia", 1986).

In further embodiments, the haploid tissue derived from an androgenic-derived, cell line, e.g., a maize microspore, is an embryo or callus tissue. In further embodiment, the methods provided may or may not go through a callus formation stage. The haploid embryos may be placed on a "non-callus promoting medium". The term "non-callus promoting medium" refers to a medium that does not support proliferation of dedifferentiated masses of cells or tissue. A preferred "non-callus promoting medium" is used for embryo rescue, containing typical salt and vitamin formulations well known in the art. Such embryo rescue, or embryo culture, media contain little or no auxin (for review see Raghaven, V., 1986, *Biol. Rev.,* 41:1-58). In some embodiments, embryo maturation medium also represents another preferred "non-callus promoting medium". Embryo maturation medium is used to promote development of in-vitro cultured embryos, preventing precocious germination, and typically contain standard salt/vitamin formulations (depending on the species), increased sugar levels and/or exogenously added abscisic acid, with little or no auxin. Another type of medium is used for shoot culture, or multiple shoot proliferation. This multiple-shoot medium can again contain little or reduced auxin, but instead contain elevated levels of cytokinin that promote meristem proliferation and growth.

Anther culture has been employed to obtain microspore-derived callus, embryos and plants in well over 200 species (Maheshwari et al., 1982, "Haploids from Pollen Grains-Retrospect and Prospect", *Amer. J. Bot.,* 69:865-879). However, the anther culture responsiveness varies considerably among species. The highest yield of responding anthers (anthers forming embryos and/or callus per 100 anthers plated) was found to be 87 percent in wheat (A. M. Wei, 1982, "Pollen Callus Culture in Triticumaertivum", *Theor. Appl. Genet.,* 63, pp. 71-73), 67 percent in rice (S. L. Lin and H. S. Tsay, 1983, *J. Agr. Res., China,* cited in Dunwell, 1985), 17 percent in maize (Ting et al., 1981, "Improved Anther Culture of Maize" (*Zea mays* L.), *Plant Science Lett.,* 23, pp. 139-145) and 1 percent in barley (Z. H. Xu and N. Sunderland, 1982, "Innoculation Density in the Culture of Barley Anthers", *Scient. Sinic.,* 25, pp. 961-968). In rye, 43 developing structures per 100 anthers were observed (G. Wenzel et al., 1977, "Increased Induction and Chromosome Doubling of Androgenetic Haploid Rye", *Theor. Appl. Genet.,* 51, pp. 81-86). Frequencies of calli producing green plant per 100 cultured anthers are in wheat 72 percent (J. W. Ouyang et al., 1983, "The Response of Anther Culture to Temperature in Triticum Aestivum", *Theor. Appl. Genet.,* 66, pp. 101-109), in rice 12 percent (L. J. Chen et al., "Medium Evaluation for Rice Anther Culture", in A. Fujiwara (ed.), "Plant Tissue Culture", pp. 551-551. Jap. Assoc. Plant Tissue Culture Tokyo, 1982) and in barley 10 percent (K. N. Kao, "Plant Formation from Barley Anther Cultures with Ficoll Media", Z. Pflanzenzuchtg., 103, 1981, pp. 437-443).

In a further embodiment, the microspore is from maize having elite performance characteristics. In an aspect of the embodiment, the microspore is from hybrid maize derived from crossing an elite maize line with a different maize line having high microspore culture response As provided in U.S. Pat. No. 5,306,864 (herein, incorporated by reference in its entirety) and U.S. Pat. No. 5,602,310 (herein, incorporated by reference in its entirety) the use of anther culture as a means of haploid breeding in maize (*Zea mays* L.) is readily applicable to different maize genotypes, including elite performance lines. Processes that allow for identifying maize germplasm which exhibit enhanced response to anther culture can be transferable to increase anther culturability in other select genotypes. Such processes are readily known in the art, and can be utilized to convert maize germplasm, including elite performance lines, into plants that produce high levels of haploid and/or dihaploid tissue cultures from cultured anthers and/or microspores.

Chromosome Doubling

In one embodiment, any of the disclosed methods of producing a haploid plant tissue with a modified haploid tissue genome further includes treating the modified haploid tissue with a chromosome doubling agent to produce a dihaploid plant tissue. In certain embodiments, the dihaploid tissue thus produced comprises a genome that is homozygous for the modification (e.g., the integrated donor polynucleotide or mutation) that was generated in the haploid genome. In a further embodiment, the maize tissue comprising the modified dihaploid genome is propagated into a mature plant that is homozygous for the genomic modification.

Methods of chromosome doubling are disclosed in Antoine-Michard, S. et at, Plant cell, tissue organ cult., Cordrecht, the Netherlands, Kluwer Academic Publishers, 1907, 48(3):203-207; Kato, A., Maize Genetics Cooperation Newsletter 1897, 38-37; and Wan, Y. et al., Theor. Appl. Genet., 1980, 77:889-892, Wan, Y, et al., Theor. Appl. Genet., 1991, 81:205-211. The disclosures of which are incorporated herein by reference. Typical methods involve contacting the cells with colchicine, anti-microtubule agents or anti-microtubule herbicides, pronamide, nitrous oxide, or any mitotic inhibitor to create homozygous doubled haploid cells. Other agents may be used with the mitotic inhibitors to improve doubling efficiency. Such agents may be dimethyl sulfoxide (DMSO), adjuvants, surfactants, and the like.

Additional chromosome doubling agents are known in the art, chemicals listed in the U.S. Pat. No. 5,866,513, herein incorporated by reference in its entirety, are applicable for use in generating dihaploid plants. Furthermore, Table 1 lists various known chromosome doubling agents.

TABLE 1

| Chromosome doubling agents. | | |
|---|---|---|
| Common Name | CAS | IUPAC |
| Colchicine and Colchicine Derivatives | | |
| Colchicine/ acetyltrimethylcol- chicinic acid colchicine derivatives | | (S)-N-(5,6,7,9-tetrahydro-1,2,3,10- tetramethoxy-9-oxobenzo (a) heptalen-7-yl) acetamide |
| Carbamates | | |
| Carbetamide | (R)-1- (ethylcarbamoyl)ethyl carbanilate | (2R)-N-ethyl-2- [[(phenylamino)carbonyl]oxy]pro- panamide |
| Chloropropham propham | | |
| Benzamides | | |
| Pronamide/ propyzamide | 3,5-dichloro-N-(1,1- dimethylpropynyl)benz- amide | 3,5-dichloro-N-(1,1-dimethyl-2- propynyl)benzamide |
| Tebutam | | |
| Benzoic Acids | | |
| Chlorthal dimethyl (DCPA), Dicamba/dianat/ disugran (dicamba- methyl) (BANVEL ™, CLARITY ™) | 3,6-dichloro-o-anisic acid | 3,6-dichloro-2-methoxybenzoic acid |
| Dinitroaniline chromosome doubling agents | | |
| Benfluralin/benefin/ (BALAN ™) | N-butyl-N-ethyl-α,α,α- trifluoro-2,6-dinitro-p- toluidine | N-butyl-N-ethyl-2,6-dinitro-4- (trifluoromethyl)benzenamine |
| Butralin | (RS)-N-sec-butyl-4-tert- butyl-2,6-dinitroaniline | 4-(1,1-dimethylethyl)-N-(1- methylpropyl)-2,6- dinitrobenzenamine |
| Chloralin | | |
| Dinitramine | N1,N1-diethyl-2,6-dinitro- 4-trifluoromethyl-m- phenylenediamine | N3,N3-diethyl-2,4-dinitro-6 (trifluoromethyl)-1,3- benzenediamine |
| Ethalfluralin (Sonalan ™) | N-ethyl-α,α,α-trifluoro-N- (2-methylallyl)-2,6-dinitro- p-toluidine | N-ethyl-N-(2-methyl-2-propenyl)- 2,6-dinitro-4- (trifluoromethyl)benzamine |
| Fluchloralin | N-(2-chloroethyl)-2,6- dinitro-N-propyl-4- (trifluoromethypaniline or N-(2-chloroethyl)-α,α,α- trifluoro-2,6-dinitro-N- propyl-p-toluidine | N-(2-chloroethyl-2,6-dinitro-N- propyl-4- (trifluoromethyl)benzenamine |

TABLE 1-continued

| Chromosome doubling agents. | | |
| --- | --- | --- |
| Common Name | CAS | IUPAC |
| Isopropalin | 4-isopropyl-2,6-dinitro-N,N-dipropylaniline | 4-(1-methylethyl)-2,6-dinitro-N,N-dipropylbenzenamine |
| Methalpropalin | α,α,α-trifluoro-N-(2-methylallyl)-2,6-dinitro-N-propyl-p-toluidine | N-(2-methyl-2-propenyl)-2,6-dinitro-N-propyl-4-(trifluoromethyl)benzenamine |
| Nitralin | 4-methylsulfonyl-2,6-dinitro-N,N-dipropylaniline | 4-(methylsulfonyl)-2,6-dinitro-N,N-dipropylbenzenamine |
| Oryzalin (SURFLAN ™) | 3,5-dinitro-N4,N4-dipropylsulfanilamide | 4-(dipropylamino)-3,5-dinitrobenzenesulfonamide |
| Pendimethalin (PROWL ™) | N-(1-ethylpropyl)-2,6-dinitro-3,4-xylidine | N-(1-ethylpropyl)-3,4-dimethyl-2,6-dinitrobenzenamine |
| Prodiamine | 5-dipropylamino-α,α,α-trifluoro-4,6-dinitro-o-toluidine or 2,6-dinitro-N1,N1-dipropyl-4-trifluoromethyl-m-phenylenediamine | 2,4-dinitro-N3,N3-dipropyl-6-(trifluoromethyl)-1,3-benzenediamine |
| Profluralin | N-cyclopropylmethyl-α,α,α-trifluoro-2,6-dinitro-N-propyl-p-toluidine or N-cyclopropylmethyl-2,6-dinitro-N-propyl-4-trifluoromethylaniline | N-(cyclopropylmethyl)-2,6-dinitro-N-propyl-4-(trifluoromethyl)benzenamine |
| Trifluralin (TREFLAN ™, TRIFIC ™, TRILLIN ™) | α,α,α-trifluoro-2,6-dinitro-N,N-dipropyl-p-toluidine | 2,6-dinitro-N,N-dipropyl-4-(trifluoromethyl)benzenamine |
| | Phosphoroamidates | |
| AMP (Amiprofos methyl ™); amiprophos-methyl | | |
| Butamifos | O-ethyl O-6-nitro-m-tolyl (RS)-sec-butylphosphoramidothioate | O-ethyl O-(5-methyl-2-nitrophenyl) (1-methylpropyl)phosphoramidothioate |
| | Pyridines | |
| Dithiopyr | methyl 2-difluoromethyl-5-(4,5-dihydro-1,3-thiazol-2-yl)-4-isobutyl-6-trifluoromethylnicotinate | methyl 2-(difluoromethyl)-5-(4,5-dihydro-2-thiazolyl)-4-(2-methylpropyl)-6-(trifluoromethyl)-3-pyridinecarboxylate |
| Thiazopyr | trifluoromethylnicotinate | pyridinecarboxylate |

In an embodiment, suitable dosage for the chromosome doubling agents for the seedling soak method disclosed herein include for example 0.01 μM, 0.5 μM, 1 μM, 2 μM, 3 μM, 4 μM, 5 μM, 10 μM, 15 μM, 20 μM, 25 μM, 30 μM, 35 μM, 40 μM, 45 μM, 50 μM, 60 μM, 70 μM, 80 μM, 90 μM, 100 μM, 125 μM, 150 μM, 200 μM, 500 μM, and 1000 μM. Suitable ranges also include for example, 0.1-10 μM, 1-100 μM, 5-125 μM, 25-200 μM, 50-500 μM, 15-150 μM and 1-10,000 μM.

In another embodiment, the chromosome doubling agent can range from 0.01%-0.5% of the solution used in the seedling soak method. For example, 0.01%, 0.02%, 0.025%, 0.05%, 0.075%, 0.1%, 0.125%, 0.15%, 0.175%, 0.2%, 0.225%, 0.25%, 0.275%, 0.3%, 0.325%, 0.35%, 0.375%, 0.4%, 0.425%, 0.45%, 0.475%, or 0.5% of the chromosome doubling agent may be used to double the chromosomes.

In further embodiments, the low seedling mortality of the chromosome doubling agents disclosed herein, when compared to colchicine (e.g., at 0.025%) can range for example from less than 10% to about 40% or less than about 5% to about 20% or less than about 15% to about 25% or less than 50% of the total number of seedlings or plant cells treated.

In other embodiments, suitable dosage for the chromosome doubling agents for the seedling foliar application method disclosed herein include for example 3.5 g ai/ha, 70 g ai/ha, 140 g ai/ha, 280 g ai/ha. Suitable application rates ranges include for example 5 g ai/ha to 1120 g ai/ha, and more preferably to 2,800 g ai/ha.

The phrase "contacting" includes reference to "direct contact" and "indirect contact." For example, the medium comprising a doubling agent may have direct contact with the haploid cell or the medium comprising the doubling agent may be separated from the haploid cell by a barrier such as a filter paper, plant tissue, or other cells thus the doubling agent is transferred through the filter paper or cells or tissue to the haploid cell. Contacting is achieved in any suitable manner, e.g., hydroponic treatment of roots, spraying, injecting, infiltrating, soaking, and wetting.

Haploid cells, haploid embryos, haploid seeds, haploid seedlings or haploid plants can be treated with a chromosome doubling agent. Homozygous plants can be regenerated from haploid cells by contacting the haploid cells, such as haploid embryo cells, with chromosome doubling agents. The haploid cells may come in contact with the doubling agent for any amount of time. In an embodiment the haploid cells are in contact with the doubling agent for 1 minute, 2 minutes, 5 minutes, 10 minutes, 15 minutes, 20 minutes, 25 minutes, 30 minutes, 35 minutes, 45 minutes, 1 hour, 2 hours, 5 hours, 10 hours, 24 hours, or 48 hours.

The haploid embryo may be isolated. It may be contained within the kernel, ovule, or seed, it may also be on the ear in the ears of maize, or on the spike as in the case of other grains such as wheat. The ear comprising: the haploid embryo may be on the plant or isolated from the plant. The ear also may be sectioned. After chromosome doubling, the doubled haploid embryo will contain 2 Copies of maternally derived chromosomes. The efficiency of the process for obtaining doubled haploid plants from haploid embryos may be greater than 10%, 20%, 30%, 50%, 60%, 70%, 80%, or 90%.

Plant Transformation

The disclosed methods of the disclosure include plant transformation methods. Plant transformation methods that can be used in the methods of the disclosure include, but are not limited to, site-specific microparticle bombardment, *Agrobacterium* transformation method, calcium phosphate transformation method, polybrene transformation method, electroporation transformation method, ultrasonic transformation method, liposome transformation method, microinjection transformation method, naked DNA transformation method, plasmid vector transformation method, viral vector transformation method, silicon carbide mediated transformation method, aerosol beaming transformation method, or PEG transformation method. Generally any plant transformation method can be used to insert DNA or any other polynucleotide sequence into the genome of a host cell. Thus, any method that provides for efficient transformation/transfection may be employed.

Numerous methods for plant transformation have been developed, including biological and physical transformation protocols for dicotyledonous plants as well as monocotyledonous plants (e.g., Goto-Fumiyuki et al., Nature Biotech 17:282-286 (1999); Miki et al., Methods in Plant Molecular Biology and Biotechnology, Glick, B. R. and Thompson, J. E. Eds., CRC Press, Inc., Boca Raton, pp. 67-88 (1993)). In addition, vectors comprising gene expression cassettes and in vitro culture methods for plant cell or tissue transformation and regeneration of plants are available, for example, in Gruber et al., Methods in Plant Molecular Biology and Biotechnology, Glick, B. R. and Thompson, J. E. Eds., CRC Press, Inc., Boca Raton, pp. 89-119 (1993).

A large number of techniques are available for inserting DNA comprising a gene expression cassette into a plant host cell. Those techniques include transformation with disarmed T-DNA using *Agrobacterium tumefaciens* or *Agrobacterium rhizogenes* as the transformation agent, calcium phosphate transfection, polybrene transformation, protoplast fusion, electroporation, ultrasonic methods (e.g., sonoporation), liposome transformation, microinjection, naked DNA, plasmid vectors, viral vectors, biolistics (microparticle bombardment), silicon carbide WHISKERS™ mediated transformation, aerosol beaming, or Poly Ethylene Glycol mediated transformation as well as other possible methods.

For example, the DNA construct comprising a gene expression cassette may be introduced directly into the genomic DNA of the plant cell using techniques such as electroporation and microinjection of plant cell protoplasts. Such plant transformation methods include, for example, protoplast transformation through calcium chloride precipitation, poly ethylene glycol (PEG) or electroporation-mediated uptake of DNA (see Paszkowski et al. (1984) *EMBO J* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505).

DNA constructs can be introduced directly to plant tissue using biolistic methods, such as DNA particle bombardment (see, e.g., Klein et al. (1987) *Nature* 327:70-73). Biolistic methods include microprojectile-mediated transformation wherein DNA is carried on the surface of microprojectiles. In this method, the expression vector is introduced into plant tissues with a biolistic device that accelerates the microprojectiles to speeds sufficient to penetrate plant cell walls and membranes. Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992).

Additional methods for plant cell transformation include microinjection via silicon carbide WHISKERS™ mediated DNA uptake (Kaeppler et al. (1990) *Plant Cell Reporter* 9:415-418). Alternatively, the DNA construct can be introduced into the plant cell via nanoparticle transformation (see, e.g., U.S. patent application Ser. No. 12/245,685, which is incorporated herein by reference in its entirety).

A widely utilized method for introducing an vector comprising a gene expression cassette into plants is based on the natural transformation system of *Agrobacterium*. Horsch et al., *Science* 227:1229 (1985). *A. tumefaciens* and *A. rhizogenes* are plant pathogenic soil bacteria known to be useful to genetically transform plant cells. The Ti and Ri plasmids of *A. tumefaciens* and *A. rhizogenes*, respectively, carry genes responsible for genetic transformation of the plant. Kado, C. I., *Crit. Rev. Plant. Sci.* 10:1 (1991). Descriptions of *Agrobacterium* vector systems and methods for *Agrobacterium*-mediated gene transfer are also available, for example, Gruber et al., supra, Miki et al., supra, Moloney et al., *Plant Cell Reports* 8:238 (1989), and U.S. Pat. Nos. 4,940,838 and 5,464,763.

When *Agrobacterium* is used for plant transformation, the DNA to be inserted can be cloned into a special plasmid referred to as an intermediate vector or into a binary vector. Intermediate vectors cannot replicate in *Agrobacterium* in the absence of a helper plasmid (conjugation). The Japan Tobacco Superbinary system is an example of such a system (see review by Komari et al., (2006) In: Methods in Molecular Biology No. 343: *Agrobacterium* Protocols ($2^{nd}$ Edition, Vol. 1) (K. Wang, ed.) HUMANA PRESS Inc., Totowa, NJ, pp. 15-41; and Komori et al., (2007) Plant Physiol. 145: 1155-1160).

Binary vectors can replicate in both *E. coli* and in *Agrobacterium*. They comprise a selection marker gene and a linker or polylinker which are framed by the right and left T-DNA border regions. Binary vectors can be transformed directly into *Agrobacterium* (Holsters, 1978). The *Agrobacterium* can be used as a host cell comprising a plasmid, e.g., the Ti or RI plasmid carrying a vir region which, typically, is necessary for the transfer of the T-DNA into the plant cell.

The virulence of an *Agrobacterium tumefaciens* host can be used to direct the insertion of a T-strand containing donor DNA into the haploid tissue or cell that is infected by *Agrobacterium* binary T DNA vector technology (Bevan (1984) *Nuc. Acid Res.* 12:8711-8721) or the co-cultivation procedure (Horsch et al. (1985) *Science* 227:1229-1231). Generally, the *Agrobacterium* transformation system is used to engineer dicotyledonous plants (Bevan et al. (1982) *Ann. Rev. Genet* 16:357-384; Rogers et al. (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al. (1984) *EMBO J* 3:3039-3041; Hooykass-Van Slogteren et al. (1984) *Nature* 311: 763-764; Grimsley et al. (1987) *Nature* 325:1677-179; Boulton et al. (1989) *Plant Mol. Biol.* 12:31-40; and Gould et al. (1991) *Plant Physiol.* 95:426-434.

Following introduction of the genetic construct comprising a gene expression cassette by plant transformation, plant cells can be grown and upon emergence of differentiating tissue such as shoots and roots, mature plants can be generated. In some embodiments, a plurality of plants can be generated. Methodologies for regenerating plants are known to those of ordinary skill in the art and can be found, for example, in: Plant Cell and Tissue Culture, 1994, Vasil and Thorpe Eds. Kluwer Academic Publishers and in: Plant Cell Culture Protocols (Methods in Molecular Biology 111, 1999 Hall Eds Humana Press). The genetically modified plant described herein can be cultured in a fermentation medium or grown in a suitable medium such as soil. In some embodiments, a suitable growth medium for higher plants can include any growth medium for plants, including, but not limited to, soil, sand, any other particulate media that support root growth (e.g., vermiculite, perlite, etc.) or hydroponic culture, as well as suitable light, water and nutritional supplements which optimize the growth of the higher plant.

Transformed plant cells which are produced by any of the above plant transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al. (1987) *Ann. Rev. of Plant Phys.* 38:467-486.

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or gfp genes) that may be present on the recombinant nucleic acid constructs. Selection and screening methodologies are well known to those skilled in the art.

The term transgenic "event" refers to a recombinant plant produced by transformation and regeneration of a single plant cell with heterologous DNA, for example, an expression cassette that includes a transgene of interest. The term "event" refers to the original transformant and/or progeny of the transformant that includes the heterologous DNA. The term "event" also refers to progeny produced by a sexual outcross between the transformant and another plant. Even after repeated backcrossing to a recurrent parent, the inserted DNA and the flanking DNA from the transformed parent is present in the progeny of the cross at the same chromosomal location. Normally, transformation of plant tissue produces multiple events, each of which represent insertion of a DNA construct into a different location in the genome of a plant cell. Based on the expression of the transgene or other desirable characteristics, a particular event is selected. In embodiments of the subject disclosure the particular event comprises a donor DNA polynucleotide inserted within a targeted genomic locus.

As used herein, "insert DNA" refers to the heterologous DNA such as a transgene within the donor DNA polynucleotide, which can comprise a gene expression cassette used to transform the plant material while "flanking DNA" or "junction DNA" can comprise either genomic DNA naturally present in an organism such as a plant, or foreign (heterologous) DNA introduced via the transformation process which is extraneous to the insert DNA molecule, e.g. fragments associated with the transformation event. A "junction" or "flanking region" or "flanking sequence" as used herein refers to a sequence of at least 20, 50, 100, 200, 300, 400, 1000, 1500, 2000, 2500, or 5000 base pair or greater which is located either immediately upstream of and contiguous with or immediately downstream of and contiguous with the insert DNA molecule.

Transformed haploid embryos which are derived by any of the above transformation techniques can be cultured to regenerate a whole plant which possesses the transformed genotype. Such regeneration techniques are called embryo rescue. Embryo rescue media can comprise certain phytohormones and energy sources or just energy sources. The growth medium may also contain a selection agent such as a biocide and/or herbicide. This selection agent can be used to indicate a marker which has been introduced through the transformation process. The transformation and regeneration of maize has been described in, for example, Gordon-Kamm et al., The Plant Cell 2:603-618 (1990).

Generation of embryos into plants is well known in the art. Embryo rescue techniques can be used to generate immature doubled haploid embryos into plants is also known (Recent Research Developments in Genetics & Breeding. Vol. 1, Part II, 237-303 2004). The disclosure of which is herein incorporated by reference.

Vectors and Donor Polynucleotides

In an embodiment, the subject disclosure relates to the introduction of one or more donor DNA polynucleotides which are inserted within a targeted genome locus. In some embodiments the donor polynucleotides comprise coding sequence. The coding sequence can encode, for example, a gene (e.g., a transgene) that confers an agronomic trait. In further embodiments, the agronomic trait is selected from the group including a insecticidal resistance trait, herbicide tolerance trait, nitrogen use efficiency trait, water use efficiency trait, nutritional quality trait, DNA binding trait, and selectable marker trait. In additional embodiments, the donor polynucleotides are expressed within the plant. An embodiment of the subject disclosure includes a plant comprising one or more donor polynucleotides. In an aspect of the embodiment, the plant comprises a haploid genome. In another aspect of the embodiment, the plant comprises a dihaploid genome.

In some embodiments, the donor polynucleotide comprises a gene expression cassette. Standard recombinant DNA and molecular cloning techniques for the construction of a gene expression cassette as used here are well known in the art and are described, e.g., by Sambrook et al., *Molecular Cloning: A Laboratory Manual*, Second Edition, Cold Spring Harbor Laboratory Press, Cold Spring Harbor, NY (1989); and by Silhavy et al., *Experiments with Gene Fusions*, Cold Spring Harbor Laboratory Press, Cold Spring Harbor, NY (1984); and by Ausubel et al., *Current Protocols in Molecular Biology*, published by Greene Publishing Assoc. and Wiley-Interscience (1987).

A number of promoters that direct expression of a gene in a plant can be employed in a donor polynucleotide. Such promoters can be selected from constitutive, chemically-regulated, inducible, tissue-specific, and seed-preferred promoters. The promoter used to direct expression of a nucleic acid depends on the particular application. For example, a strong constitutive promoter suited to the host cell is typically used for expression and purification of expressed proteins.

Non-limiting examples of plant promoters include promoter sequences derived from *A. thaliana* ubiquitin-10 (ubi-10) (Callis, et al., 1990, *J. Biol. Chem.*, 265:12486-12493); *A. tumefaciens* mannopine synthase (Δmas) (Petolino et al., U.S. Pat. No. 6,730,824); and/or Cassava Vein Mosaic Virus (CsVMV) (Verdaguer et al., 1996, Plant Molecular Biology 31:1129-1139). Other constitutive promoters include, for example, the core Cauliflower Mosaic Virus 35S promoter (Odell et al. (1985) Nature 313:810-812); Rice Actin promoter (McElroy et al. (1990) Plant Cell 2:163-171); Maize Ubiquitin promoter (U.S. Pat. No. 5,510,474; Christensen et al. (1989) Plant Mol. Biol. 12:619-632 and Christensen et al. (1992) Plant Mol. Biol. 18:675-689); pEMU promoter (Last et al. (1991) Theor. Appl. Genet. 81:581-588); ALS promoter (U.S. Pat. No. 5,659,026); Maize Histone promoter (Chabouté et al. Plant Molecular Biology, 8:179-191 (1987)); and the like.

Other useful plant promoters include tissue specific and inducible promoters. An inducible promoter is one that is capable of directly or indirectly activating transcription of one or more DNA sequences or genes in response to an inducer. In the absence of an inducer the DNA sequences or genes will not be transcribed. Typically, the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. Typically the protein factor that binds specifically to an inducible regulatory element to activate transcription is present in an inactive form which is then directly or indirectly converted to the active form by the inducer. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory element may be exposed to an inducer by externally applying the inducer to the cell or plant such as by spraying, watering, heating or similar methods.

Any inducible promoter can be used in the embodiments of the instant disclosure. See Ward et al., Plant Mol. Biol. 22: 361-366 (1993). Exemplary inducible promoters include ecdysone receptor promoters (U.S. Pat. No. 6,504,082); promoters from the ACE1 system which respond to copper (Mett et al., Proc. Natl. Acad. Sci. 90: 4567-4571 (1993)); In2-1 and In2-2 gene from maize which respond to benzenesulfonamide herbicide safeners (U.S. Pat. No. 5,364,780; Hershey et al., Mol. Gen. Genetics 227: 229-237 (1991) and Gatz et al., Mol. Gen. Genetics 243: 32-38 (1994)); Tet repressor from Tn10 (Gatz et al., Mol. Gen. Genet. 227: 229-237 (1991); or promoters from a steroid hormone gene, the transcriptional activity of which is induced by a glucocorticosteroid hormone, Schena et al., Proc. Natl. Acad. Sci. U.S.A. 88: 10421 (1991) and McNellis et al., (1998) Plant J. 14(2):247-257; the maize GST promoter, which is activated by hydrophobic electrophilic compounds that are used as pre-emergent herbicides (see U.S. Pat. No. 5,965,387 and International Patent Application, Publication No. WO 93/001294); and the tobacco PR-1a promoter, which is activated by salicylic acid (see Ono S, Kusama M, Ogura R, Hiratsuka K., "Evaluation of the Use of the Tobacco PR-1a Promoter to Monitor Defense Gene Expression by the Luciferase Bioluminescence Reporter System," Biosci Biotechnol Biochem. 2011 Sep. 23; 75(9):1796-800). Other chemical-regulated promoters of interest include tetracycline-inducible and tetracycline-repressible promoters (see, for example, Gatz et al., (1991) Mol. Gen. Genet. 227:229-237, and U.S. Pat. Nos. 5,814,618 and 5,789,156).

Other regulatable promoters of interest include a cold responsive regulatory element or a heat shock regulatory element, the transcription of which can be effected in response to exposure to cold or heat, respectively (Takahashi et al., Plant Physiol. 99:383-390, 1992); the promoter of the alcohol dehydrogenase gene (Gerlach et al., PNAS USA 79:2981-2985 (1982); Walker et al., PNAS 84(19):6624-6628 (1987)), inducible by anaerobic conditions; and the light-inducible promoter derived from the pea rbcS gene or pea psaDb gene (Yamamoto et al., (1997) Plant J. 12(2): 255-265); a light-inducible regulatory element (Feinbaum et al., Mol. Gen. Genet. 226:449, 1991; Lam and Chua, Science 248:471, 1990; Matsuoka et al. (1993) Proc. Natl. Acad. Sci. USA 90(20):9586-9590; Orozco et al. (1993) Plant Mol. Bio. 23(6):1129-1138), a plant hormone inducible regulatory element (Yamaguchi-Shinozaki et al., Plant Mol. Biol. 15:905, 1990; Kares et al., Plant Mol. Biol. 15:225, 1990), and the like. An inducible regulatory element also can be the promoter of the maize In2-1 or In2-2 gene, which responds to benzenesulfonamide herbicide safeners (Hershey et al., Mol. Gen. Gene. 227:229-237, 1991; Gatz et al., Mol. Gen. Genet. 243:32-38, 1994), and the Tet repressor of transposon Tn10 (Gatz et al., Mol. Gen. Genet. 227:229-237, 1991). Stress inducible promoters include salt/water stress-inducible promoters such as PSCS (Zang et al., (1997) Plant Sciences 129:81-89); cold-inducible promoters, such as, cor15a (Hajela et al., (1990) Plant Physiol. 93:1246-1252), cor15b (Wilhelm et al., (1993) Plant Mol Biol 23:1073-1077), wsc1 (Ouellet et al., (1998) FEBS Lett. 423-324-328), ci7 (Kirch et al., (1997) Plant Mol Biol. 33:897-909), ci21A (Schneider et al., (1997) Plant Physiol. 113:335-45); drought-inducible promoters, such as Trg-31 (Chaudhary et al., (1996) Plant Mol. Biol. 30:1247-57), rd29 (Kasuga et al., (1999) Nature Biotechnology 18:287-291); osmotic inducible promoters, such as Rab17 (Vilardell et al., (1991) Plant Mol. Biol. 17:985-93) and osmotin (Raghothama et al., (1993) Plant Mol Biol 23:1117-28); and heat inducible promoters, such as heat shock proteins (Barros et al., (1992) Plant Mol. 19:665-75; Marrs et al., (1993) Dev. Genet. 14:27-41), smHSP (Waters et al., (1996) J. Experimental Botany 47:325-338), and the heat-shock inducible element from the parsley ubiquitin promoter (WO 03/102198). Other stress-inducible promoters include rip2 (U.S. Pat. No. 5,332,808 and U.S. Publication No. 2003/0217393) and rd29a (Yamaguchi-Shinozaki et al., (1993) Mol. Gen. Genetics 236:331-340). Certain promoters are inducible by wounding, including the *Agrobacterium* pMAS promoter (Guevara-Garcia et al., (1993) Plant J. 4(3):495-505) and the *Agrobacterium* ORF13 promoter (Hansen et al., (1997) Mol. Gen. Genet. 254(3):337-343).

Tissue-preferred promoters can be utilized to target enhanced transcription and/or expression within a particular plant tissue. When referring to preferential expression, what is meant is expression at a higher level in the particular plant tissue than in other plant tissue. Examples of these types of promoters include seed preferred expression such as that provided by the phaseolin promoter (Bustos et al., (1989) *The Plant Cell* Vol. 1, 839-853), and the maize globulin-1 gene (Belanger, et al. (1991) *Genetics* 129:863-972). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa zein, γ-zein, waxy, shrunken 1, shrunken 2, globulin 1, etc. Seed-preferred promoters also include those promoters that direct gene expression predominantly to specific tissues within the seed such as, for example, the endosperm-preferred promoter of γ-zein, the cryptic promoter from tobacco (Fobert et al., (1994) T-DNA tagging of a seed coat-specific cryptic promoter in tobacco. Plant J. 4: 567-577), the P-gene promoter from maize (Chopra et al., (1996) Alleles of the maize P gene with distinct tissue specificities encode Myb-homologous proteins with C-terminal replacements. Plant Cell 7:1149-1158, Erratum in Plant Cell. 1997, 1:109), the globulin-1 promoter from maize (Belenger and Kriz (1991) Molecular basis for Allelic Polymorphism of the maize Globulin-1 gene. Genetics 129: 863-972), and promoters that direct expression to the seed coat or hull of maize kernels, for example the pericarp-specific glutamine synthetase promoter (Muhitch et al., (2002) Isolation of a Promoter Sequence From the Glutamine Synthetase$_{1-2}$ Gene Capable of Conferring Tissue-Specific Gene Expression in Transgenic Maize. Plant Science 163:865-872).

In addition to the promoter, the expression cassette (which can be in, e.g., a vector) typically contains a transcription unit or expression cassette that contains all the additional elements required for the expression of the nucleic acid in host cells, either prokaryotic or eukaryotic. A typical expression cassette thus contains a promoter operably linked to a nucleic acid sequence encoding a gene product (e.g., a protein). The expression cassette may also include additional elements which are operably linked according to methods known art: signals required for efficient polyadenylation of the transcript, transcriptional termination, ribosome binding sites, or translation termination. Additionally, the expression cassette may include enhancers and/or heterologous splicing signals.

Other components of the donor polynucleotide or vector may be included, also depending upon intended use of the donor polynucleotide. Examples include selectable markers, targeting or regulatory sequences, transit peptide sequences such as the optimized transit peptide sequence (see U.S. Pat. No. 5,510,471) stabilizing sequences such as RB7 MAR (see Thompson and Myatt, (1997) *Plant Mol. Biol.,* 34: 687-692 and International Patent Publication No. WO9727207) or leader sequences, introns etc. General descriptions and examples of plant expression vectors and reporter genes can be found in Gruber, et al., "Vectors for Plant Transformation" in *Methods in Plant Molecular Biology and Biotechnology*, Glick et al eds; CRC Press pp. 89-119 (1993). The selection of an appropriate expression vector will depend upon the host and the method of introducing the expression vector into the host. The expression cassette will also include at the 3' terminus of the heterologous nucleotide sequence of interest, a transcriptional and translational termination region functional in plants. The termination region can be native with the promoter nucleotide sequence of embodiments of the present disclosure, can be native with the DNA sequence of interest, or can be derived from another source. Convenient termination regions are available from the Ti-plasmid of *A. tumefaciens*, such as the octopine synthase and nopaline synthase (nos) termination regions (Depicker et al., Mol. and Appl. Genet. 1:561-573 (1982) and Shaw et al. (1984) Nucleic Acids Research vol. 12, No. 20 pp 7831-7846(nos)); see also Guerineau et al. Mol. Gen. Genet. 262:141-144 (1991); Proudfoot, Cell 64:671-674 (1991); Sanfacon et al. Genes Dev. 5:141-149 (1991); Mogen et al. Plant Cell 2:1261-1272 (1990); Munroe et al. Gene 91:151-158 (1990); Ballas et al., Nucleic Acids Res. 17:7891-7903 (1989); Joshi et al. Nucleic Acid Res. 15:9627-9639 (1987).

The expression cassettes can additionally contain 5' leader sequences. Such leader sequences can act to enhance translation. Translation leaders are known in the art and include by way of example, picornavirus leaders, EMCV leader (Encephalomyocarditis 5' noncoding region), Elroy-Stein et al., Proc. Nat. Acad. Sci. USA 86:6126-6130 (1989); potyvirus leaders, for example, TEV leader (Tobacco Etch Virus) Carrington and Freed Journal of Virology, 64:1590-1597 (1990), MDMV leader (Maize Dwarf Mosaic Virus), Allison et al., Virology 154:9-20 (1986); human immunoglobulin heavy-chain binding protein (BiP), Macejak et al., Nature 353:90-94 (1991); untranslated leader from the coat protein mRNA of alfalfa mosaic virus (AMV RNA 4), Jobling et al., Nature 325:622-625 (1987); Tobacco mosaic virus leader (TMV), Gallie et al., (1989) Molecular Biology of RNA, pages 237-256; and maize chlorotic mottle virus leader (MCMV) Lommel et al., Virology 81:382-385 (1991). See also Della-Cioppa et al., Plant Physiology 84:965-968 (1987).

The expression cassette construct can also contain sequences that enhance translation and/or mRNA stability such as introns. An example is the first intron of gene II of the histone H3.III variant of *Arabidopsis thaliana*. Chaubet et al., Journal of Molecular Biology, 225:569-574 (1992).

In those instances where it is desirable for the expression cassette to express a gene product that is directed to a particular organelle, particularly the plastid, amyloplast, or to the endoplasmic reticulum, or secreted at the cell's surface or extracellularly, the expression cassette can further comprise a coding sequence for a transit peptide. Such transit peptides are well known in the art and include, but are not limited to, the transit peptide for the acyl carrier protein, the small subunit of RUBISCO, plant EPSP synthase and *Helianthus annuus* (U.S. Pat. No. 5,510,417), *Zea mays* Brittle-1 chloroplast transit peptide (Nelson et al., Plant Physiol 117(4):1235-1252 (1998); Sullivan et al., Plant Cell 3(12):1337-48; Sullivan et al., Planta (1995) 196(3):477-84; Sullivan et al., J. Biol. Chem. (1992) 267(26):18999-9004) and the like. In addition, chimeric chloroplast transit peptides are known in the art, such as the Optimized Transit Peptide (U.S. Pat. No. 5,510,471). Additional chloroplast transit peptides have been described previously in U.S. Pat. Nos. 5,717,084 and 5,728,925. One skilled in the art will readily appreciate the many options available in expressing a product to a particular organelle. For example, the barley alpha amylase sequence is often used to direct expression to the endoplasmic reticulum (Rogers, J. Biol. Chem. 260: 3731-3738 (1985)).

It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of post-translational modifications. Additionally, the promoter sequence might be genetically engineered to improve the level of expression as compared to the native promoter. Recombinant techniques useful for controlling the expression of nucleic acid molecules include, but are not limited to, stable integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno or Kozak sequences), modification of nucleic acid molecules to correspond to the codon usage of the host cell, and deletion of sequences that destabilize transcripts.

Reporter or marker genes for selection of transformed cells or tissues or plant parts or plants can be included in the transformation vectors. Examples of selectable markers include those that confer resistance to anti-metabolites such as herbicides or antibiotics, for example, dihydrofolate reductase, which confers resistance to methotrexate (Reiss, Plant Physiol. (Life Sci. Adv.) 13:143-149, 1994; see also Herrera Estrella et al., Nature 303:209-213, (1983); Meijer et al., Plant Mol. Biol. 16:807-820, (1991)); neomycin phosphotransferase, which confers resistance to the aminoglycosides neomycin, kanamycin and paromycin (Herrera-Estrella, EMBO J. 2:987-995, 1983 and Fraley et al., Proc. Natl. Acad. Sci USA 80:4803 (1983)) and hygromycin phosphotransferase, which confers resistance to hygromycin (Marsh, Gene 32:481-485, (1984); see also Waldron et al., Plant Mol. Biol. 5:103-108, (1985); Zhijian et al., Plant Science 108:219-227, (1995)); trpB, which allows cells to utilize indole in place of tryptophan; hisD, which allows cells to utilize histinol in place of histidine (Hartman, Proc. Natl. Acad. Sci., USA 85:8047, (1988)); mannose-6-phosphate isomerase which allows cells to utilize mannose (International Patent Application No. WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology*, Cold Spring Harbor Laboratory ed.); and deaminase from *Aspergillus terreus*, which confers resistance to Blasticidin S (Tamura, Biosci. Biotechnol. Biochem. 59:2336-2338, (1995)).

Additional selectable markers include, for example, a mutant acetolactate synthase, which confers imidazolinone or sulfonylurea resistance (Lee et al., EMBO J. 7:1241-1248, (1988)), a mutant psbA, which confers resistance to atrazine (Smeda et al., Plant Physiol. 103:911-917, (1993)), or a mutant protoporphyrinogen oxidase (see U.S. Pat. No. 5,767,373), or other markers conferring resistance to an herbicide such as glufosinate. Examples of suitable selectable marker genes include, but are not limited to, genes encoding resistance to chloramphenicol (Herrera Estrella et al., EMBO J. 2:987-992, (1983)); streptomycin (Jones et al., Mol. Gen. Genet. 210:86-91, (1987)); spectinomycin (Bretagne-Sagnard et al., Transgenic Res. 5:131-137, (1996)); bleomycin (Hille et al., Plant Mol. Biol. 7:171-176, (1990)); sulfonamide (Guerineau et al., Plant Mol. Biol. 15:127-136, (1990)); bromoxynil (Stalker et al., Science 242:419-423, (1988)); glyphosate (Shaw et al., Science 233:478-481, (1986)); phosphinothricin (DeBlock et al., EMBO J. 6:2513-2518, (1987)), and the like.

One option for use of a selective gene is a glufosinate-resistance encoding DNA and in one embodiment can be the phosphinothricin acetyl transferase (pat), maize optimized pat gene or bar gene under the control of the Cassava Vein Mosaic Virus promoter. These genes confer resistance to bialaphos. See, (see, Wohlleben et al., (1988) Gene 70: 25-37); Gordon-Kamm et al., Plant Cell 2:603; 1990; Uchimiya et al., BioTechnology 11:835, 1993; White et al., Nucl. Acids Res. 18:1062, 1990; Spencer et al., Theor. Appl. Genet. 79:625-631, 1990; and Anzai et al., Mol. Gen. Gen. 219:492, 1989). A version of the pat gene is the maize optimized pat gene, described in U.S. Pat. No. 6,096,947.

In addition, markers that facilitate identification of a plant cell containing the polynucleotide encoding the marker may be employed. Scorable or screenable markers are useful, where presence of the sequence produces a measurable product and can produce the product without destruction of the plant cell. Examples include a β-glucuronidase, or uidA gene (GUS), which encodes an enzyme for which various chromogenic substrates are known (for example, U.S. Pat. Nos. 5,268,463 and 5,599,670); chloramphenicol acetyl transferase (Jefferson et al. The EMBO Journal vol. 6 No. 13 pp. 3901-3907); and alkaline phosphatase. In a preferred embodiment, the marker used is beta-carotene or provitamin A (Ye et al., Science 287:303-305-(2000)). The gene has been used to enhance the nutrition of rice, but in this instance it is employed instead as a screenable marker, and the presence of the gene linked to a gene of interest is detected by the golden color provided. Unlike the situation where the gene is used for its nutritional contribution to the plant, a smaller amount of the protein suffices for marking purposes. Other screenable markers include the anthocyanin/flavonoid genes in general (See discussion at Taylor and Briggs, The Plant Cell (1990)2:115-127) including, for example, a R-locus gene, which encodes a product that regulates the production of anthocyanin pigments (red color) in plant tissues (Dellaporta et al., in *Chromosome Structure and Function*, Kluwer Academic Publishers, Appels and Gustafson eds., pp. 263-282 (1988)); the genes which control biosynthesis of flavonoid pigments, such as the maize C1 gene (Kao et al., Plant Cell (1996) 8: 1171-1179; Scheffler et al., Mol. Gen. Genet. (1994) 242:40-48) and maize C2 (Wienand et al., Mol. Gen. Genet. (1986) 203:202-207); the B gene (Chandler et al., Plant Cell (1989) 1:1175-1183), the p1 gene (Grotewold et al., Proc. Natl. Acad. Sci USA (1991) 88:4587-4591; Grotewold et al., Cell (1994) 76:543-553; Sidorenko et al., Plant Mol. Biol. (1999)39:11-19); the bronze locus genes (Ralston et al., Genetics (1988) 119:185-197; Nash et al., Plant Cell (1990) 2(11): 1039-1049), among others.

Further examples of suitable markers include the cyan fluorescent protein (CYP) gene (Bolte et al., (2004) J. Cell Science 117: 943-54 and Kato et al., (2002) Plant Physiol 129: 913-42), the yellow fluorescent protein gene (PHIYFP™ from Evrogen; see Bolte et al., (2004) J. Cell Science 117: 943-54); a lux gene, which encodes a luciferase, the presence of which may be detected using, for example, X-ray film, scintillation counting, fluorescent spectrophotometry, low-light video cameras, photon counting cameras or multiwell luminometry (Teeri et al. (1989) EMBO J. 8:343); a green fluorescent protein (GFP) gene (Sheen et al., Plant J. (1995) 8(5):777-84); and DsRed2 where plant cells transformed with the marker gene are red in color, and thus visually selectable (Dietrich et al., (2002) Biotechniques 2(2):286-293). Additional examples include a β-lactamase gene (Sutcliffe, Proc. Nat'l. Acad. Sci. U.S.A. (1978) 75:3737), which encodes an enzyme for which various chromogenic substrates are known (e.g., PADAC, a chromogenic cephalosporin); a xylE gene (Zukowsky et al., Proc. Nat'l. Acad. Sci. U.S.A. (1983) 80:1101), which encodes a catechol dioxygenase that can convert chromogenic catechols; an α-amylase gene (Ikuta et al., Biotech.

(1990) 8:241); and a tyrosinase gene (Katz et al., J. Gen. Microbiol. (1983) 129:2703), which encodes an enzyme capable of oxidizing tyrosine to DOPA and dopaquinone, which in turn condenses to form the easily detectable compound melanin. Clearly, many such markers are available and known to one skilled in the art.

In certain embodiments, the nucleotide sequence of the transgene encoding a gene product in an expression cassette can be optionally combined with another nucleotide sequence of interest in the cassette and/or the plant. The term "nucleotide sequence of interest" refers to a nucleic acid molecule (which may also be referred to as a polynucleotide) which can be a transcribed RNA molecule as well as DNA molecule, that encodes for a desired polypeptide or protein, but also may refer to nucleic acid molecules that do not constitute an entire gene, and which do not necessarily encode a polypeptide or protein (e.g., a promoter). For example, in certain embodiments the transgene can be combined or "stacked" with another nucleotide sequence of interest that provides additional resistance or tolerance to glyphosate or another herbicide, and/or provides resistance to select insects or diseases and/or nutritional enhancements, and/or improved agronomic characteristics, and/or proteins or other products useful in feed, food, industrial, pharmaceutical or other uses. The "stacking" of two or more nucleic acid sequences of interest within a plant genome can be accomplished, for example, via conventional plant breeding using two or more events, transformation of a plant with a construct which contains the sequences of interest, re-transformation of a transgenic plant, or addition of new traits through targeted integration via homologous recombination.

Such nucleotide sequences of interest include, but are not limited to, those examples of genes or coding sequences that confer (1) resistance to pests or disease, (2) resistance to herbicides, and (3) value added traits provided below:

1. Genes or Coding Sequences (e.g. iRNA) That Confer Resistance to Pests or Disease (A) Plant Disease Resistance Genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. Examples of such genes include, the tomato Cf-9 gene for resistance to *Cladosporium falvum* (Jones et al., 1994 Science 266:789), tomato Pto gene, which encodes a protein kinase, for resistance to *Pseudomonas syringae* pv. tomato (Martin et al., 1993 Science 262:1432), and *Arabidopsis* RSSP2 gene for resistance to *Pseudomonas syringae* (Mindrinos et al., 1994 Cell 78:1089).

(B) A *Bacillus thuringiensis* protein, a derivative thereof or a synthetic polypeptide modeled thereon, such as, a nucleotide sequence of a Bt δ-endotoxin gene (Geiser et al., 1986 Gene 48:109), and a vegetative insecticidal (VIP) gene (see, e.g., Estruch et al., (1996) Proc. Natl. Acad. Sci. 93:5389-94). Moreover, DNA molecules encoding δ-endotoxin genes can be purchased from American Type Culture Collection (Rockville, Md.), under ATCC accession numbers 40098, 67136, 31995 and 31998.

(C) A lectin, such as, nucleotide sequences of several *Clivia miniata* mannose-binding lectin genes (Van Damme et al., 1994 Plant Molec. Biol. 24:825).

(D) A vitamin binding protein, such as avidin and avidin homologs which are useful as larvicides against insect pests. See U.S. Pat. No. 5,659,026.

(E) An enzyme inhibitor, e.g., a protease inhibitor or an amylase inhibitor. Examples of such genes include a rice cysteine proteinase inhibitor (Abe et al., 1987 J. Biol. Chem. 262:16793), a tobacco proteinase inhibitor I (Huub et al., 1993 Plant Molec. Biol. 21:985), and an α-amylase inhibitor (Sumitani et al., 1993 Biosci. Biotech. Biochem. 57:1243).

(F) An insect-specific hormone or pheromone such as an ecdysteroid and juvenile hormone a variant thereof, a mimetic based thereon, or an antagonist or agonist thereof, such as baculovirus expression of cloned juvenile hormone esterase, an inactivator of juvenile hormone (Hammock et al., 1990 Nature 344:458).

(G) An insect-specific peptide or neuropeptide which, upon expression, disrupts the physiology of the affected pest (J. Biol. Chem. 269:9). Examples of such genes include an insect diuretic hormone receptor (Regan, 1994), an allostatin identified in Diploptera punctata (Pratt, 1989), and insect-specific, paralytic neurotoxins (U.S. Pat. No. 5,266,361).

(H) An insect-specific venom produced in nature by a snake, a wasp, etc., such as a scorpion insectotoxic peptide (Pang, (1992) Gene 116:165).

(I) An enzyme responsible for a hyperaccumulation of monoterpene, a sesquiterpene, a steroid, hydroxamic acid, a phenylpropanoid derivative or another non-protein molecule with insecticidal activity.

(J) An enzyme involved in the modification, including the post-translational modification, of a biologically active molecule; for example, glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. Examples of such genes include, a callas gene (PCT published application WO93/02197), chitinase-encoding sequences (which can be obtained, for example, from the ATCC under accession numbers 3999637 and 67152), tobacco hookworm chitinase (Kramer et al., (1993) Insect Molec. Biol. 23:691), and parsley ubi4-2 polyubiquitin gene (Kawalleck et al., (1993) Plant Molec. Biol. 21:673).

(K) A molecule that stimulates signal transduction. Examples of such molecules include nucleotide sequences for mung bean calmodulin cDNA clones (Botella et al., (1994) Plant Molec. Biol. 24:757) and a nucleotide sequence of a maize calmodulin cDNA clone (Griess et al., (1994) Plant Physiol. 104:1467).

(L) A hydrophobic moment peptide. See U.S. Pat. Nos. 5,659,026 and 5,607,914; the latter teaches synthetic antimicrobial peptides that confer disease resistance.

(M) A membrane permease, a channel former or a channel blocker, such as a cecropin-β lytic peptide analog (Jaynes et al., (1993) Plant Sci. 89:43) which renders transgenic tobacco plants resistant to *Pseudomonas solanacearum.*

(N) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. See, for example, Beachy et al., (1990) Ann. Rev. Phytopathol. 28:451.

(O) An insect-specific antibody or an immunotoxin derived therefrom. Thus, an antibody targeted to a critical metabolic function in the insect gut would inactivate an affected enzyme, killing the insect. For example, Taylor et al., (1994) Abstract #497, Seventh Int'l. Symposium on Molecular Plant-Microbe Interactions shows enzymatic inactivation in transgenic tobacco via production of single-chain antibody fragments.

(P) A virus-specific antibody. See, for example, Tavlado-raki et al., (1993) Nature 266:469, which shows that trans-genic plants expressing recombinant antibody genes are protected from virus attack.

(Q) A developmental-arrestive protein produced in nature by a pathogen or a parasite. Thus, fungal endo α-1,4-D polygalacturonases facilitate fungal colonization and plant nutrient release by solubilizing plant cell wall homo-α-1,4-D-galacturonase (Lamb et al., (1992) Bio/Technology 10:1436). The cloning and characterization of a gene which encodes a bean endopolygalacturonase-inhibiting protein is described by (Toubart et al., (1992) Plant J. 2:367).

(R) A developmental-arrestive protein produced in nature by a plant, such as the barley ribosome-inactivating gene that provides an increased resistance to fungal disease (Longemann et al., (1992). Bio/Technology 10:3305).

(S) RNA interference, in which a DNA polynucleotide encoding an RNA molecule is used to inhibit expression of a target gene. An RNA molecule in one example is partially or fully double stranded, which triggers a silencing response, resulting in cleavage of dsRNA into small interfering RNAs, which are then incorporated into a targeting complex that destroys homologous mRNAs. See, e.g., Fire et al., U.S. Pat. No. 6,506,559; Graham et al., U.S. Pat. No. 6,573,099.

2. Genes or Coding Sequences that Confer Resistance to a Herbicide (A) Genes encoding resistance or tolerance to a herbicide that inhibits the growing point or meristem, such as an imidazalinone, sulfonanilide or sulfonylurea herbicide. Exemplary genes in this category code for a mutant ALS enzyme (Lee et al., (1988) EMBO J. 7:1241), which is also known as AHAS enzyme (Miki et al., (1990) Theor. Appl. Genet. 80:449).

(B) One or more additional genes encoding resistance or tolerance to glyphosate imparted by mutant EPSP synthase and aroA genes, or through metabolic inactivation by genes such as GAT (glyphosate acetyltransferase) or GOX (gly-phosate oxidase) and other phosphono compounds such as glufosinate (pat and bar genes; DSM-2), and aryloxyphe-noxypropionic acids and cyclohexanediones (ACCase inhibitor encoding genes). See, for example, U.S. Pat. No. 4,940,835, which discloses the nucleotide sequence of a form of EPSP which can confer glyphosate resistance. A DNA molecule encoding a mutant aroA gene can be obtained under ATCC Accession Number 39256, and the nucleotide sequence of the mutant gene is disclosed in U.S. Pat. No. 4,769,061. European Patent application No. 0 333 033 and U.S. Pat. No. 4,975,374 disclose nucleotide sequences of glutamine synthetase genes which confer resis-tance to herbicides such as L-phosphinothricin. The nucleo-tide sequence of a phosphinothricin acetyltransferase gene is provided in European Patent application No. 0 242 246. De Greef et al., (1989) Bio/Technology 7:61 describes the production of transgenic plants that express chimeric bar genes coding for phosphinothricin acetyl transferase activ-ity. Exemplary of genes conferring resistance to aryloxy-phenoxypropionic acids and cyclohexanediones, such as sethoxydim and haloxyfop, are the Accl-S1, Accl-S2 and Accl-S3 genes described by Marshall et al., (1992) Theor. Appl. Genet. 83:435.

(C) Genes encoding resistance or tolerance to a herbicide that inhibits photosynthesis, such as a triazine (psbA and gs+ genes) and a benzonitrile (nitrilase gene). Przibilla et al., (1991) Plant Cell 3:169 describe the use of plasmids encoding mutant psbA genes to transform *Chlamydomonas*. Nucleotide sequences for nitrilase genes are disclosed in U.S. Pat. No. 4,810,648, and DNA molecules containing these genes are available under ATCC accession numbers 53435, 67441 and 67442. Cloning and expression of DNA coding for a glutathione S-transferase is described by Hayes et al., (1992) Biochem. J. 285:173.

(D) Genes encoding resistance or tolerance to a herbicide that bind to hydroxyphenylpyruvate dioxygenases (HPPD), enzymes which catalyze the reaction in which para-hydroxy-phenylpyruvate (HPP) is transformed into homogentisate. This includes herbicides such as isoxazoles (European Pat-ent No. 418175, European Patent No. 470856, European Patent No. 487352, European Patent No. 527036, European Patent No. 560482, European Patent No. 682659, U.S. Pat. No. 5,424,276), in particular isoxaflutole, which is a selec-tive herbicide for maize, diketonitriles (European Patent No. 496630, and European Patent No. 496631), in particular 2-cyano-3-cyclopropyl-1-(2-SO2CH3-4-CF3 phenyl) pro-pane-1,3-dione and 2-cyano-3-cyclopropyl-1-(2-SO2CH3-4-2,3Cl2phenyl) propane-1,3-dione, triketones (European Patent No. 625505, European Patent No. 625508, U.S. Pat. No. 5,506,195), in particular sulcotrione, and pyrazolinates. A gene that produces an overabundance of HPPD in plants can provide tolerance or resistance to such herbicides, including, for example, genes described in U.S. Pat. Nos. 6,268,549 and 6,245,968 and U.S. Patent Application, Pub-lication No. 20030066102.

(E) Genes encoding resistance or tolerance to phenoxy auxin herbicides, such as 2,4-dichlorophenoxyacetic acid (2,4-D) and which may also confer resistance or tolerance to aryloxyphenoxypropionate (AOPP) herbicides. Examples of such genes include the α-ketoglutarate-dependent dioxy-genase enzyme (aad-1) gene, described in U.S. Pat. No. 7,838,733.

(F) Genes encoding resistance or tolerance to phenoxy auxin herbicides, such as 2,4-dichlorophenoxyacetic acid (2,4-D) and which may also confer resistance or tolerance to pyridyloxy auxin herbicides, such as fluroxypyr or triclopyr. Examples of such genes include the α-ketoglutarate-depen-dent dioxygenase enzyme gene (aad-12), described in WO 2007/053482 A2.

(G) Genes encoding resistance or tolerance to dicamba (see, e.g., U.S. Patent Publication No. 20030135879).

(H) Genes providing resistance or tolerance to herbicides that inhibit protoporphyrinogen oxidase (PPO) (see U.S. Pat. No. 5,767,373).

(I) Genes providing resistance or tolerance to triazine herbicides (such as atrazine) and urea derivatives (such as diuron) herbicides which bind to core proteins of photosys-tem II reaction centers (PS II) (See Brussian et al., (1989) EMBO J. 1989, 8(4): 1237-1245.

3. Genes That Confer or Contribute to a Value-Added Trait (A) Modified fatty acid metabolism, for example, by transforming maize or *Brassica* with an antisense gene or stearoyl-ACP desaturase to increase stearic acid content of the plant (Knultzon et al., (1992) Proc. Nat. Acad. Sci. USA 89:2624.

(B) Decreased phytate content.

(1) Introduction of a phytase-encoding gene, such as the *Aspergillus niger* phytase gene (Van Hartingsveldt et al., (1993) Gene 127:87), enhances breakdown of phytate, add-ing more free phosphate to the transformed plant.

(2) A gene could be introduced that reduces phytate content. In maize, this, for example, could be accomplished by cloning and then reintroducing DNA associated with the single allele which is responsible for maize mutants characterized by low levels of phytic acid (Raboy et al., (1990) Maydica 35:383).

(C) Modified carbohydrate composition effected, for example, by transforming plants with a gene coding for an enzyme that alters the branching pattern of starch. Examples of such enzymes include, *Streptococcus mucus* fructosyltransferase gene (Shiroza et al., (1988) J. Bacteriol. 170: 810), *Bacillus subtilis* levansucrase gene (Steinmetz et al., (1985) Mol. Gen. Genel. 200:220), *Bacillus licheniformis* α-amylase (Pen et al., (1992) Bio/Technology 10:292), tomato invertase genes (Elliot et al., (1993), barley amylase gene (Sogaard et al., (1993) J. Biol. Chem. 268:22480), and maize endosperm starch branching enzyme II (Fisher et al., (1993) Plant Physiol. 102:10450).

Site-Specific Nuclease

In embodiments, the methods and compositions described herein make use of one or more site-specific nucleases. The disclosed methods comprise delivering one or more polynucleotides encoding site-specific nucleases to transformation-competent haploid tissue derived from maize microspore. These site specific nucleases can modify genomic DNA by cleaving the DNA or inducing DNA breaks, which can be double-stranded breaks or single-stranded breaks. Embodiments of site-specific nucleases include a TALEN, a meganuclease, a CRISPR-nuclease, or a Zinc Finger Nuclease.

In one embodiment, the site-specific nuclease used in the disclosed methods is an engineered (non-naturally occurring) TALEN nuclease. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al (2007) *Science* 318:648-651). These proteins contain a TAL-effector DNA binding domain and a transcriptional activation domain. One of the most well characterized TAL-effectors is AvrBs3 from *Xanthomonas campestgris* pv. *Vesicatoria* (see Bonas et al (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3): 256-272). In the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences of the tandem repeats domain. In certain examples, each repeated sequence comprises approximately 102 bp; and the repeats are typically 91-100% homologous with each other (Bonas et al, ibid). The repeats typically include a polymorphism, which is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target).

In another embodiment, the site-specific nuclease used in the methods of the disclosure can be engineered to include a (non-naturally occurring) meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-30 3388; Dujon et al. (1989) *Gene* 82:115-118; Perler et al. (1994) Nucleic Acids Res. 22, 11127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 5 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In further embodiments, the site-specific nuclease used in the disclosed methods is an engineered (non-naturally occurring) CRISPR nuclease. The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas nuclease (e.g., Cas9) to a region homologous to the crRNA in the target DNA called a "protospacer". The Cas nuclease cleaves the DNA to generate blunt ends at the DSB at sites specified by a guide sequence contained within the crRNA transcript. Cas9 requires both the crRNA and the tracrRNA for site-specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al (2012) Science 337, p. 816-821, Jinek et al, (2013), eLife 2:e00471, and David Segal, (2013) eLife 2:e00563). Thus, the CRISPR/Cas system can be engineered to create a double-stranded break (DSB) at a desired target in a genome, and repair of the DSB can be influenced by the use of repair inhibitors to cause an increase in error prone repair.

In certain embodiments, Cas nuclease may be a "functional derivative" of a naturally occurring Cas nuclease. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a nuclease activity in common with a corresponding native sequence polypeptide. The nuclease activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas nuclease or a nuclease fragment thereof include but are not limited to mutants, fusions, covalent modifications of Cas protein or a nuclease fragment thereof. Cas nuclease, or functional derivatives thereof, may be obtainable from a cell or synthesized chemically or by a combination of these two procedures. The cell may be a cell that naturally produces Cas nuclease, or a cell that naturally produces Cas nuclease and is genetically engineered to produce the endogenous Cas protein at a higher expression level or to produce a Cas nuclease from an exogenously introduced nucleic acid, which nucleic acid encodes a Cas nuclease that is same or different from the endogenous Cas. In some case, the cell does not naturally produce Cas protein and is genetically engineered to produce a Cas nuclease. The Cas nuclease is deployed in mammalian cells (and putatively within plant cells) by co-expressing the Cas nuclease with guide RNA. Two forms of guide RNAs can be used to facilitate Cas-mediated genome cleavage as disclosed in Le Cong, F., et al., (2013) Science 339(6121):819-823.

In certain embodiments, the DNA binding domain of one or more of the nucleases used for in vivo cleavage and/or targeted cleavage of the genome of a cell comprises a zinc finger protein. In some embodiments, the zinc finger protein is non-naturally occurring and is engineered to bind to a target site of choice. See, for example, Beerli et al. (2002) Nature Biotechnol. 20:135-141; Pabo et al. (2001) Ann. Rev. Biochem. 70:313-340; Isalan et al. (2001) Nature Biotechnol. 19:656-660; Segal et al. (2001) Curr. Opin. Biotechnol. 12:632-637; Choo et al. (2000) Curr. Opin. Struct. Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Selection of target sites; ZFPs and methods for design and construction of fusion proteins (and polynucleotides encoding same) are known to those of skill in the art and described in detail in U.S. Pat. Nos. 6,140,815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

Thus, in the methods for integrating a donor polynucleotide disclosed herein, the site-specific nuclease comprises a DNA-binding domain that specifically binds to a target site at a locus in the maize genome into which it is desired to insert the donor DNA polynucleotide (which can comprise at least one transgene).

Any suitable cleavage domain can be operatively linked to a DNA-binding domain to form a nuclease fusion protein. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) Proc Natl Acad Sci USA 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014275. Likewise, TALEN DNA-binding domains have been fused to nuclease domains to create TALENs. See, e.g., U.S. Publication No. 20110301073.

As noted above, the cleavage domain may be heterologous to the DNA-binding domain, for example a zinc finger DNA-binding domain and a cleavage domain from a different nuclease or a TALEN DNA-binding domain and a cleavage domain from a different nuclease, or a meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, MA; and Belfort et al. (1997) Nucleic Acids Res. 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) Nucleases, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al., (1998) Proc. Natl. Acad. Sci. USA 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a Fok I cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Patent Application Publication WO 07/014275, incorporated herein in its entirety. Additional restriction enzymes also contain separable binding and cleavage domains, and these are contemplated by the present disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987; 20070305346 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains.

Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E: I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes. In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055). In other embodiments, the engineered cleavage half domain comprises the "Sharkey" and/or "Sharkey" mutations (see Guo et al, (2010) J. Mol. Biol. 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see, e.g., U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014275. Expression of the nuclease may be under the control of a constitutive promoter or an inducible promoter.

A "target" or "target site" or "targeted genomic locus" or "genomic DNA target region" is a nucleic acid sequence that defines a portion of a nucleic acid to which a binding molecule (e.g. site-specific nuclease) will bind, provided sufficient conditions for binding exist.

In an embodiment a genomic locus sequence includes those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic locus sequences can be normal (i.e., wild-type) or mutant; mutant sequences can comprise, for example, insertions (e.g., previously inserted exogenous polynucleotides), deletions, translocations, rearrangements, and/or point mutations. A genomic locus sequence can also comprise one of a number of different alleles.

Also described herein as an embodiment of the disclosure are methods for inserting a donor DNA polynucleotide sequence within a genomic loci. Reported and observed frequencies of targeted genomic modification indicate that targeting of a genomic loci within plants is relatively inefficient. The success rate of such methods are low, due in part to poor efficiency of homologous recombination and a high frequency of non-specific insertion of the donor DNA into regions of the genome other than the target site. The present disclosure provides methods for identifying a donor DNA polynucleotide within a targeted genomic loci.

Disclosed herein are methods of using site-specific nucleases (e.g., engineered zinc finger binding domains fused to cleavage domains) to generate one or more targeted double-stranded breaks in cellular DNA. Although the disclosed methods do not depend on a particular mechanism of action, it is known that double-stranded breaks in cellular DNA stimulate cellular repair mechanisms several thousand-fold in the vicinity of the cleavage site, such targeted cleavage allows for the alteration or replacement (via homology-directed repair) of sequences at virtually any site in the genome.

In addition to the use of site-specific nucleases described herein, targeted replacement of (or insertion into) a selected genomic sequence also requires the introduction of donor DNA polynucleotide. The donor DNA polynucleotide can be introduced into the cell prior to, concurrently with, or subsequent to, expression of the site-specific nuclease(s). The donor DNA polynucleotide contains sufficient homology to a genomic sequence to support homologous recombination (or homology-directed repair) between donor DNA polynucleotide and the homologous genomic sequence. Approximately 25, 50 100, 200, 500, 750, 1,000, 1,500, 2,000 nucleotides or more of sequence homology between a donor DNA polynucleotide and a genomic locus (or any integral value between 10 and 2,000 nucleotides, or more) will support homologous recombination therebetween. Donor DNA polynucleotide sequences can range in length from 10 to 5,000 nucleotides (or any integral value of nucleotides therebetween) or longer. The donor DNA polynucleotide sequence need not be identical to the genomic sequence that it replaces. For example, the sequence of the donor DNA polynucleotide can contain one or more single base changes, insertions, deletions, inversions or rearrangements with respect to the genomic sequence, so long as sufficient homology with chromosomal sequences is present. Alternatively, a donor DNA polynucleotide sequence can contain a non-homologous sequence flanked by two regions of homology. Additionally, donor DNA polynucleotide sequences can comprise a vector molecule containing sequences that are not homologous to the region of interest in cellular chromatin. Generally, the homologous region(s) of a donor DNA polynucleotide sequence has at least 50% sequence identity to a genomic locus with which recombination is desired. In certain embodiments, donor DNA polynucleotide sequence has 60%, 70%, 80%, 85%, 90%, 95%, 98%, 99%, or 99.9% sequence identity over a span of 25 or more, 50 or more, 100 or more, 200 or more, 300 or more, 400 or more, 500 or more, 750 or more, 1,000 or more, 1,500 or more, or 2,000 or more nucleotides of sequence homology between a donor DNA polynucleotide and the genomic locus.

A donor DNA polynucleotide molecule can contain two or more, discontinuous regions of homology to cellular chromatin. For example, for targeted insertion of transgene sequences not normally present in a genomic region of interest, such a transgene sequence can be flanked by regions of homology to the genomic region of interest in the donor DNA polynucleotide.

In other embodiments, targeted replacement of a selected genomic sequence also requires the introduction of the replacement or donor DNA polynucleotide sequence within the targeted genomic locus via a non-homologous end joining mechanism (NHEJ). Subsequently, the donor strand does not require homologous arms for integration of the donor polynucleotide sequence. As a result of a double strand break within a targeted genomic locus, the donor polynucleotide sequence is integrated within the chromosome. The NHEJ repair pathway provides another alternative mechanism for integrating a donor polynucleotide within the genome. See WO2013169802, herein incorporated by reference.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al., (1987) Proc. Natl Acad. Sd. USA 84:4959-4963; Nehls et al., (1996) Science 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A donor DNA polynucleotide can be introduced into a cell as part of a vector molecule having additional sequences such as, for example, replication origins, promoters and genes encoding antibiotic resistance. Moreover, donor DNA polynucleotides can be introduced as naked nucleic acid, as nucleic acid complexed with an agent such as a liposome or poloxamer or can be delivered by bacteria or viruses (e.g., *Agrobacterium* sp., *Rhizobium* sp. NGR234, *Sinorhizoboium meliloti, Mesorhizobium loti*, tobacco mosaic virus, potato virus X, cauliflower mosaic virus and cassava vein mosaic virus. See, e.g., Chung et al. (2006) Trends Plant Sd. 11(1): 1-4). In further embodiments, donor DNA polynucleotide can be introduced into a cell (e.g., in androgenic callus tissue) by a microparticle bombardment transformation method as described herein.

Applicants' methods can combine the powerful targeting capabilities of engineered ZFPs with a cleavage domain (or cleavage half-domain) to specifically target a double-stranded break to the region of the genome at insertion of exogenous sequences is desired. Although not required by Applicants' methods, it appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular {e.g., genomic or chromosomal) sequence, i.e., by a processes of homology-directed repair, also known as "gene conversion."

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. Higher homologous recombination efficiencies are typically observed when the double-stranded break is closer to the site at which recombination is desired. In cases for which a precise site of recombination is not required (e.g., the desired recombination event can occur over an interval of genomic sequence), the length and sequence of the donor nucleic acid, together with the site(s) of cleavage, can be selected to obtain the desired recombination event. In cases in which the desired event is designed to change the sequence of a single nucleotide in a genomic sequence, cellular chromatin is cleaved within 10,000 nucleotides on either side of the nucleotide. For example, cleavage can occur within any integral value between 2 and 1,000 of nucleotides on either side of the nucleotide. In certain examples, cleavage occurs within 1,000, 500, 200, 100, 90, 80, 70, 60, 50, 40, 30, 20, 10, 5, or 2 nucleotides on either side of the nucleotide that is changed in the genomic sequence.

As detailed above, the binding sites for two fusion proteins, each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

In certain embodiments, a homologous chromosome can serve as the donor DNA polynucleotide. Thus, for example, correction of a mutation in a heterozygote can be achieved by engineering fusion proteins that bind to and cleave the mutant sequence on one chromosome, but do not cleave the wild-type sequence on the homologous chromosome. The double-stranded break on the mutation-bearing chromosome stimulates a homology-based "gene conversion" process in which the wild-type sequence from the homologous chromosome is copied into the cleaved chromosome, thus restoring two copies of the wild-type sequence.

Methods and compositions are also provided that may enhance levels of targeted recombination including, but not limited to, the use of additional ZFP-functional domain fusions to activate expression of genes involved in homologous recombination, such as, for example, members of the RAD52 epistasis group (e.g., Rad50, Rad51, Rad51B, RadSIC, RadSID, Rad52, Rad54, Rad54B, Mrell, XRCC2, XRCC3), genes whose products interact with the aforementioned gene products (e.g., BRCA1, BRCA2) and/or genes in the NBS1 complex. See, e.g., Boyko et al. (2006) Plant Physiology 141:488-497 and LaFarge et al. (2003) Nucleic Acids Res 31(4): 1148-1155. Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Riha et al. (2002) EMBO 21:2819-2826; Freisner et al. (2003) Plant J. 34:427-440; Chen et al. (1994) European Journal of Biochemistry 224: 135-142. Methods for activation and repression of gene expression using fusions between a zinc finger binding domain and a functional domain are disclosed, for example, in co-owned U.S. Pat. Nos. 6,534,261; 6,824,978 and 6,933, 113. Additional repression methods include the use of antisense oligonucleotides and/or small interfering RNA (siRNA or RNAi) targeted to the sequence of the gene to be repressed.

Detection Assays

In certain embodiments, the disclosure relates to a method that includes confirming a modification of genomic DNA such as the cleavage of targeted maize genome, the integration of a donor DNA polynucleotide within a targeted maize genome, or a mutation incorporated within the targeted maize genome. In certain embodiments, the method of confirming such a modification of the genome includes confirmation by a PCR based assay, Southern blot assay, Northern blot assay, protein expression assay, Western blot assay, ELISA assay, or Next Generation Sequencing assay.

Accordingly, a modification of genomic DNA such as a cleavage, integrated transgene, or a mutation in the genome can be confirmed in a variety of ways, including using a primer or probe of the sequence. In certain embodiments, the stably integrated transgene may be detected based on the constitutive or selective expression of the transgene in some tissues of the plant or at some developmental stages, or the transgene may be expressed in substantially all plant tissues, substantially along its entire life cycle.

Confirmation of a targeted genomic modification, integrated transgene, or mutation may be carried out by any suitable method of amplification. See generally, Kwoh et al., Am. Biotechnol. Lab. 8, 14-25 (1990). Examples of suitable amplification techniques include, but are not limited to, polymerase chain reaction, ligase chain reaction, strand displacement amplification (see generally G. Walker et al., Proc. Natl. Acad. Sci. USA 89, 392-396 (1992); G. Walker et al., Nucleic Acids Res. 20, 1691-1696 (1992)), transcription-based amplification (see D. Kwoh et al., Proc. Natl. Acad Sci. USA 86, 1173-1177 (1989)), self-sustained sequence replication (or "35R") (see J. Guatelli et al., Proc. Natl. Acad. Sci. USA 87, 1874-1878 (1990)), the Qβ replicase system (see P. Lizardi et al., BioTechnology 6, 1197-1202 (1988)), nucleic acid sequence-based amplification (or "NASBA") (see R. Lewis, Genetic Engineering News 12 (9), 1 (1992)), the repair chain reaction (or "RCR") (see R. Lewis, supra), and boomerang DNA amplification (or "BDA") (see R. Lewis, supra). Polymerase chain reaction is generally preferred.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity.

As used herein, the term "polymerase chain reaction" and "PCR" generally refers to the method for increasing the concentration of a segment of a target sequence in a mixture of genomic DNA without cloning or purification (U.S. Pat. Nos. 4,683,195; 4,683,202; and 4,965,188; herein incorporated by reference). This process for amplifying the target sequence comprises introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified.

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

In an embodiment, the amplification reaction is quantified. In other embodiments, the amplification reaction is quantitated using a signature profile, in which the signature profile is selected from the group including a melting temperature and a fluorescence signature profile.

The nucleic acid molecule of embodiments of the disclosure, or segments thereof, can be used as primers for PCR amplification. In performing PCR amplification, a certain degree of mismatch can be tolerated between primer and template. Therefore, mutations, deletions, and insertions (especially additions of nucleotides to the 5' or 3' end) of the exemplified primers fall within the scope of the subject disclosure. Mutations, insertions, and deletions can be produced in a given primer by methods known to an ordinarily skilled artisan.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, CA), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar assays are a method of detecting and quantifying the presence of a DNA sequence. Briefly, the genomic DNA sample comprising the targeted genomic locus is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the donor DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the donor DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group including a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. in one embodiment, a second fluorescent DNA dye is SYTO13® used at less than 10 µM, less than 4 µM, or less than 2.7 µM.

In further embodiments, Next Generation Sequencing (NGS) can be used for confirming a genomic modification. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX from 454 Life Sciences/Roche, the Illumina Genome Analyser from Solexa and Applied Biosystems' SOLiD (acronym for: 'Sequencing by Oligo Ligation and Detection'). In addition, there are two single molecule sequencing methods that are currently being developed. These include the true Single Molecule Sequencing (tSMS) from Helicos Bioscience and the Single Molecule Real Time sequencing (SMRT) from Pacific Biosciences.

The Genome Sequencher FLX which is marketed by 454 Life Sciences/Roche is a long read NGS, which uses emulsion PCR and pyrosequencing to generate sequencing reads. DNA fragments of 300-800 bp or libraries containing fragments of 3-20 kbp can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser which is marketed by Solexa is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems is a short read technology. This NGS technology uses fragmented double stranded DNA that are up to 10 kbp in length. The system uses sequencing by ligation of dye-labeled oligonucleotide primers and emulsion PCR to generate one billion short reads that result in a total sequence output of up to 30 gigabases per run.

tSMS of Helicos Bioscience and SMRT of Pacific Biosciences apply a different approach which uses single DNA molecules for the sequence reactions. The tSMS Helicos system produces up to 800 million short reads that result in 21 gigabases per run. These reactions are completed using fluorescent dye-labeled virtual terminator nucleotides that is described as a 'sequencing by synthesis' approach.

The SMRT Next Generation Sequencing system marketed by Pacific Biosciences uses a real time sequencing by synthesis. This technology can produce reads of up to 1000 bp in length as a result of not being limited by reversible terminators. Raw read throughput that is equivalent to one-fold coverage of a diploid human genome can be produced per day using this technology.

In another embodiment, the confirmation of genomic modification can be completed using blotting assays, including Western blots, Northern blots, and Southern blots. Such blotting assays are commonly used techniques in biological research for the identification and quantification of biological samples. These assays include first separating the sample components in gels by electrophoretic means, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the confirmation of a genomic modification can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

Introgression of Transgenes into Progeny Plants

The subject disclosure provides a method for introgression of a donor polynucleotide comprising a transgene from the androgenic callus-derived dihaploid plant into progeny plants. The production of dihaploid plants, including dihaploid plants that are homozygous for a transgene, are described herein. In one embodiment, the method comprises the steps of:

i) crossing a female parent plant with a male parent plant, wherein the male parent plant is the dihaploid plant, and wherein the female parent plant is a fertile parent plant;

ii) harvesting a progeny seed from the cross of (a);

iii) planting the progeny seed; and, iv) growing the progeny seed, wherein the progeny seed comprise the donor polynucleotide comprising the transgene.

In certain embodiments of the method, the female and male parent plants that are maize plants. In further embodiments the female parent plant is an elite maize plant.

Such a crossing to create progeny seed can be done using conventional plant breeding techniques. For a discussion of plant breeding techniques, see Poehlman (1995) *Breeding Field Crops*. AVI Publication Co., Westport Conn, 4$^{th}$ Edit. Backcrossing methods may be used to introduce a gene into the plants. A description of this technique and other plant breeding methodologies for introducing traits into a plant can be found in references such as Poehlman, supra, and *Plant Breeding Methodology*, edit. Neal Jensen, John Wiley & Sons, Inc. (1988). In a typical backcross protocol, the original variety of interest (recurrent parent) is crossed to a second variety (nonrecurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

Thus, this disclosure provides a processes of making maize plant that includes crosses using the dihaploid plants produced according to the methods herein. For example, the subject disclosure includes a method for producing a progeny seed by crossing a dihaploid plant (made according to the methods disclosed herein) containing donor polynucleotides with a second and genetically different plant (e.g. in-bred parent), harvesting the resultant progeny seed, and detecting the integrated donor polynucleotides using a method such as real-time PCR to determine the zygosity.

A maize plant can be bred by (i) sexually crossing a first parental maize plant, which is grown from seed of a line containing the donor polynucleotides comprising the transgene with a second parental maize plant, thereby producing a plurality of first progeny plants; (ii) then selecting a first progeny plant that contains the donor polynucleotides comprising the transgene; and (iii) selfing the first progeny plant, thereby producing a plurality of second progeny plants; and then selecting from the second progeny plants a plant that contains the donor polynucleotides comprising an agronomic trait. These steps can further include (iv) backcrossing the first progeny plant or the second progeny plant to the second parental maize plant or a third parental maize plant.

When the maize plant of the subject disclosure is crossed with another inbred plant to yield a progeny or hybrid, the original parent can serve as either the maternal or paternal plant with basically, the same characteristics in the hybrids. Occasionally, maternally inherited characteristics may express differently depending on the decision of which parent to use as the female. However, often one of the parental plants is preferred as the maternal plant because of increased seed yield and preferred production characteristics, such as optimal seed size and quality or ease of tassel removal. Some plants produce tighter ear husks leading to more loss, for example due to rot, or the ear husk may be so tight that the silk cannot completely push out of the tip preventing complete pollination resulting in lower seed yields. There can be delays in silk formation which deleteriously affect timing of the reproductive cycle for a pair of parental inbreds. Seed coat characteristics can be preferable in one plant which may affect shelf life of the hybrid seed product. Pollen can shed can be better by one plant, thus rendering that plant as the preferred male parent.

In some embodiments, the first step of "crossing" the female parent plant with the male dihaploid parent plant comprises planting, preferably in pollinating proximity, seeds of a first maize plant and a second, distinct female inbred maize plant. In some embodiments, hand-pollinating can be used to cross the male and female parents. In other embodiments, the hand-pollinating used to cross the male and female parents is performed with a tool or by mechanical means. In further embodiments, the hand-pollinating used to cross the male and female parents is performed by obtaining pollen from a male plant and applying the pollen to the stigma (by way of the pollen tube) of the female plants.

A further step comprises cultivating or growing the seeds of the female parent plant and the male parent plant that bear flowers. If the parental plants differ in timing of sexual maturity, techniques may be employed to obtain an appropriate nick, i.e., to ensure the availability of pollen from the parent maize plant designated the male during the time at which silks on the parent maize plant designated the female are receptive to the pollen. Methods that may be employed to obtain the desired nick include delaying the flowering of the faster maturing plant, such as, but not limited to delaying the planting of the faster maturing seed, cutting or burning the top leaves of the faster maturing plant (without killing the plant) or speeding up the flowering of the slower maturing plant, such as by covering the slower maturing plant with film designed to speed germination and growth or by cutting the tip of a young ear shoot to expose silk.

In certain embodiments, the female parent plant and the male parent plant are treated with one or more agricultural chemicals as considered appropriate by the grower.

A further step comprises harvesting the seeds, near or at maturity, from the ear of the plant that received the pollen. In a particular embodiment, seed is harvested from the female parent plant, and when desired, the harvested seed can be grown to produce a progeny or first generation ($F_1$) hybrid maize plant.

Yet another step comprises drying and conditioning the seeds, including the treating, sizing (or grading) of seeds, and packaging for sale to growers for the production of grain or forage. As with inbred seed, it may be desirable to treat hybrid seeds with compositions that render the seeds and seedlings grown therefrom more hardy when exposed to adverse conditions. The resulting progeny or hybrid seed may be sold to growers for the production of grain and forage and not for breeding or seed production.

Still further, the subject disclosure provides a progeny maize plant produced by growing the harvested seeds produced on the female parent plant as well as grain produced by the progeny maize plant.

In a subsequent embodiment, the disclosure provides a method of introducing a donor polynucleotide that imparts a desired trait into the progeny plant. In an aspect of the embodiment, the desired trait is selected from the group including an insecticidal resistance trait, herbicide tolerant trait, disease resistance trait, yield increase trait, nutritional quality trait, agronomic increase trait, and combinations thereof. Other examples of a desired trait include modified fatty acid metabolism, for example, by transforming a plant with an antisense gene of stearoyl-ACP desaturase to increase stearic acid content of the plant. See Knultzon et al., Proc. Natl. Acad. Sci. USA 89: 2624 (1992). Decreased phytate content: (i) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an *Aspergillus niger* phytase gene. (ii) A gene could be introduced that reduces phytate content. In maize, this, for example, could be accomplished, by cloning and then reintroducing DNA associated with the single allele which is responsible for maize mutants characterized by low levels of phytic acid. See Raboy et al., Maydica 35: 383 (1990). (iii) Modified carbohydrate composition effected, for example, by transforming plants with a gene coding for an enzyme that alters the branching pattern of starch. See Shiroza et al., J. Bacteriol. 170: 810 (1988) (nucleotide sequence of *Streptococcus mutans* fructosyl-transferase gene), Steinmetz et al., Mol. Gen. Genet. 200: 220 (1985) (nucleotide sequence of *Bacillus subtillus* levansucrase gene), Pen et al., Bio/Technology 10: 292 (1992) (production of transgenic plants that express *Bacillus licheniformis* α-amylase), Elliot et al., Plant Molec. Biol. 21: 515 (1993) (nucleotide sequences of tomato invertase genes), Sogaard et al., J. Biol. Chem. 268: 22480 (1993) (site-directed mutagenesis of barley α-amylase gene), and Fisher et al., Plant Physiol. 102: 1045 (1993) (maize endosperm starch branching enzyme II). Further examples of potentially desired characteristics include greater yield, better stalks, better roots, reduced time to crop maturity, better agronomic quality, higher nutritional value, higher starch extractability or starch fermentability, resistance and/or tolerance to insecticides, herbicides, pests, heat and drought, and disease, and uniformity in germination times, stand establishment, growth rate, maturity and kernel size.

A maize crop comprising maize seeds which contain the donor polynucleotides comprising an agronomic trait, or progeny thereof, can be rapidly detected using the method including a real-time PCR assay to determine the zygosity and then be planted. The method including a real-time PCR assay to determine the zygosity can improve the efficiency of this process.

The subject method including a real-time PCR assay to determine the zygosity is useful in, for example, maize breeding programs as well as quality control, especially for commercial production of maize seeds. This method can also benefit product registration and product stewardship. This method can be used for accelerated breeding introgression strategies. The detection techniques of the subject disclosure are especially useful in conjunction with plant breeding introgression, to determine which progeny plants comprise the donor polynucleotides comprising an agronomic trait after a parent plant containing the event is crossed with another plant line in an effort to impart the agronomic trait into the progeny. The disclosed method including a real-time PCR assay to determine the zygosity benefits maize breeding introgression programs as well as quality control, especially for commercialized maize seeds.

The present disclosure can be used for a marker assisted breeding (MAB) method. The present disclosure can be used in combination with other methods (such as, AFLP markers, RFLP markers, RAPD markers, SNPs, and SSRs) that identify genetically linked markers which are proximate to the donor polynucleotides comprising an agronomic trait. The method including a real-time PCR assay to determine the zygosity allows for tracking of the donor polynucleotides comprising an agronomic trait in the progeny of a plant-breeding cross. The method including a real-time PCR assay to determine the zygosity of the present disclosure can be used to identify any maize variety containing the donor polynucleotides comprising an agronomic trait.

It should be understood that the examples and embodiments described herein are for illustrative purposes only and that various modifications or changes in light thereof will be suggested to persons skilled in the art and are to be included within the spirit and purview of this application and the scope of the appended claims. These examples should not be construed as limiting.

EXAMPLES

Example 1. Generation of Microspore-Derived Haploid Callus

Pre-emergent tassels of the *Zea mays* genotype 139/39-05 (U.S. Pat. No. 5,306,864) were harvested from greenhouse-grown maize plants (~5-6 week-old) when the microspores were at the early binucleate stage of development (anthers ~3 mm long, bright, glossy yellow). The tassels were wrapped in moist paper towels and aluminum foil and placed into an incubator set at 8° C. for 7-14 days. Following surface sterilization (15 min in 0.08% v/v Chlorox™ followed by a sterile water rinse), anthers were aseptically isolated, placed onto the surface of liquid 'anther culture medium' (N6 salts and vitamins, 60 g/L sucrose, 5 g/L activated charcoal, 500 mg/L casein hydrolysate, 0.1 mg/L TIBA adjusted to pH 5.8) in 6-well dishes at a density of 60 anthers in 6 mL medium per well and incubated at 28° C. in the dark. Microspore-derived embryo-like structures, appearing between 14-28 days, were transferred to 'callus medium' (MS salts and vitamins, 30 g/L sucrose, 700 mg/L L-proline, 500 mg/L MES, 100 mg/L casein hydrolysate, 15 mg/L silver nitrate, 3.3 mg/L dicamba and 2.5 g/L Gelrite™ adjusted to pH 5.8). Nodular, embryogenic callus was subcultured to fresh 'callus medium' every 14 days to bulk up prior to ploidy determination and transformation.

The foregoing provides an example of androgenic transformation-competent haploid tissue derived from maize microspores, which can be used in the disclosed methods of modifying a haploid maize genome.

Example 2. Ploidy Determination of Callus

In order to determine cell ploidy level, 1 g of callus tissue made in Example 1 was transferred to a sterile Petri™ dish (Fisher Scientific, St. Louis, MO). Nuclei were released by chopping the callus tissue with a single-edged razor blade in the presence of 1-2 mL of filtered, ice cold Gailbraith buffer (0.01M $MgSO_4$, 0.005M KCl, 0.0005M HEPES, 1 mg/mL DTT) along with 'MMG medium' (4 mM MES [pH 6.0], 0.6M mannitol, 15 mM $MgCl_2$) and 0.25% Triton X-100™. The Petri™ dish was rinsed with an additional 2 mL of buffer, which was combined with the initial nuclear extract to make a final slurry volume of ~5 mL. The crude nuclear extract was then gently homogenized by transferring to a glass tissue homogenizer and pumping the plunger up and down a couple of times. The homogenate was then filtered through tea strainers and the resultant filtrate was aspirated through a 40 μm Steri-flip™ (Millipore; Billerica, Massachusetts, USA) to isolate nuclei. Isolated nuclei were stained with propidium iodide (Sigma-Aldrich; St. Louis, Missouri, USA) using 10 μL/200 μL sample and analyzed with a Beckman Quanta™ flow cytometer (Beckman-Coulter, Brea, CA, USA). For each sample, at least 50,000 nuclei were collected and 75 μL samples were fed into the cytometer for analysis using a logarithmic scale display. The flow cytometer results showed a large haploid (G0/G1) peak and a smaller diploid (G2) diploid peak. The results confirm that the callus tissue made according to Example 1 consisted of haploid cells suitable for use in the disclosed methods of modifying a haploid maize genome.

Example 3. Constructs for Targeted Genome Modification in Protoplasts Isolated from Haploid Callus For targeted genome modification, a zinc finger nuclease (ZFN) construct, pDAB111879 (depicted in FIG. 1), was used. Expression of the ZFN was driven by the maize ubi1 promoter and terminated with the maize per5 3' UTR. This expression cassette contained the "T2A" architecture comprising two zinc finger monomeric domains (zmPPL_1360-r23a1 and zmPPL_1360-30a1) encoded by, and expressed from, a single coding region. The expressed transcript included the T2A stutter signal (Mattion et al., 1996, *J. Virol.*, 70:8124-7) to introduce a ribosomal stutter that releases the first polypeptide during translation and is designed, upon further translation, to produce the first and second polypeptide in equimolar amounts. An opaque2 nuclear localization sequence (NLS) was included in both ZF monomers for targeting to the nucleus. Each of the two NLS-ZF domain fusions possesses binding specificity to the unique sequence of the maize genome show in Table 2. The zinc finger monomers also included a FokI nuclease functional domain (Kim et al., 1996, *Proc. Natl. Acad. Sci. USA*, 100:1156-1160) which was codon-biased using a monocot preferred codon table.

TABLE 2

Zinc finger binding domains and unique
sequences in the maize genome recognized
by designed zinc finger proteins.

| Zinc Finger Protein Monomer | SEQ ID NO: | Binds to DNA Sequence 5-3' |
|---|---|---|
| zmPPL_1360-r23a1 | SEQ ID NO: 1 | ACTCCGTATGCGAAGGCA |
| zmPPL_1360-30a1 | SEQ ID NO: 2 | TTCGCGGTGGGACACTTG |

Figure 2:
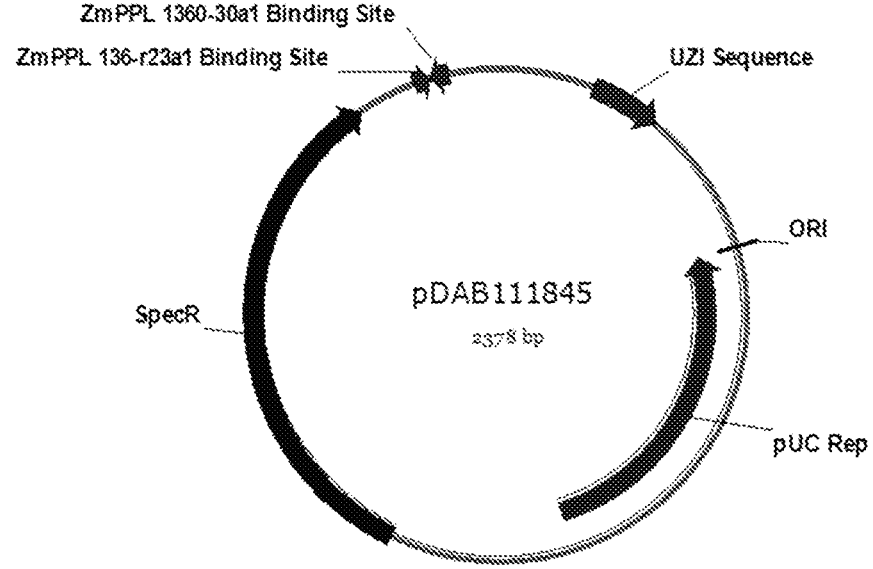
FIG. 2 provides a plasmid map of pDAB111845. This plasmid maps is of a donor construct for targeted integration in haploid protoplasts.

A donor polynucleotide construct, pDAB111845 (depicted in FIG. 2), was used for targeted DNA integration into haploid callus-derived protoplasts by site-directed double strand cleavage via the ZFN construct and subsequent DNA repair. This construct contains the DNA binding sequence for the two ZF monomers, zmPPL_1360-r23a1 and zmPPL_1360-30a1. Additionally, this construct contains a 110 bp sequence referred to as 'UZI' for use in downstream analysis, i.e., primer site design, of targeted insertion via in/out PCR. Co-delivery of this plasmid with pDAB 111879 (ZFN construct) results in cleavage at a unique genomic sequence and within the donor construct, pDAB118845, upon ZFN expression, which facilitates targeted integration of the donor construct into the genomic cleavage site via non-homologous end joining DNA repair and recombination.

The foregoing provides examples of constructs that can be used in the disclosed methods of modifying a haploid maize genome: pDAB111879 for delivery of site-specific zinc finger nucleases and pDAB111845 for targeted integration of a donor polynucleotide.

Example 4. Targeted Genome Modification in Protoplasts Isolated from Haploid Callus Haploid callus (~5 grams) was transferred to a sterile Petri™ dish and 5 mL of 'MMG medium' was added. A single-edge razor blade was used to finely slice the callus into small pieces until a creamy slurry was obtained. A sterile spatula was used to transfer the slurry to a sterile 50 mL conical tube (Fisher Scientific) and 20 mL of 'enzyme solution' (3% Cellulase™ [Onozuka R10, Yakult Pharmaceuticals, Japan], 0.3% Pectolyase™ [MP Biomedicals, San Diego, CA] dissolved in 'MMG medium'). The tubes were wrapped with Parafilm™ and placed on a Vari-Mix™ platform rocker (Thermo Scientific, Waltham, MA) and set at vigorous rocking for ~16-18 hours in the dark at 24° C. In a sterile 50 mL conical tube, the 'enzyme solution' was slowly filtered through a 100 μm cell strainer (Falcon). The cell strainer (with cells) was rinsed by pipetting 10 mL of 'W5+ medium' (1.86 mM MES [pH6.0], 0.5 mL of 0.2 M MES [pH6.0], 192 mM NaCl, 6.7 mL of 1.54 M NaCl, 154 mM CaCl₂, 8.3 mL of 1M CaCl₂, 4.7 mM KCl, 1.25 mL of 0.2M KCl and 37 mL water) through the 100 μm cell strainer. This step was repeated using a 70 μm cell strainer (Falcon) to catch smaller debris. The filtrate was then sieved using a 40 μm cell strainer (Falcon) and rinsed again with 10 mL of 'W5⁺ medium' resulting in a final filtrate volume of 40 mL. The tube was then gently inverted and 8 mL of a 'heavy gradient solution' (500 mM sucrose, 1 mM CaCl₂ and 5 mM MES [pH 6.0]) was slowly added to the filtrate beneath the protoplast/'enzyme solution'/'W5+' mixture in the tube. The tube was then centrifuged with a swing arm bucket rotor (from Eppendorf, Hauppauge, NY) for 10 minutes at 1500 rpm. The protoplast layer (visible between the 'heavy gradient solution' and the 'enzyme solution'/ 'W5+ medium') was then slowly removed using a 10 mL narrow bore pipette tip and placed in a sterile 50 mL conical tube. The tube was then brought to a volume of 35 mL using 'W5⁺ medium', slowly inverted several times and centrifuged for 10 minutes at 1000 rpm. The supernatant was then removed without disturbing the pellet. The pellet containing protoplasts was then resuspended in 5 mL of 'MMG medium'. The concentration of protoplasts per mL was determined using a Beckman Quanta™ flow cytometer by first resuspending the pellet in 5 mL of 'MMG medium' and then adding 30 μL to 270 μL of 'MMG medium' in a 96-well plate.

For transfection, protoplasts were diluted to 1.67 million per mL using 'MMG medium'. 300 μL of each sample (~500,000 protoplasts) was transferred into a sterile 2 mL tube. A total of 40 μg of plasmid DNA (36 μg of pDAB 111845 [donor polynucleotide]+4 μg of pDAB111879 [ZFN-encoding polynucleotide]) was added to each tube and slowly mixed by inverting the tubes and incubated for 5 minutes at room temperature. PEG4000™ (Sigma-Aldrich, St. Louis, MO) was slowly added (300 μL) to the protoplast/ DNA mixture and gently inverted until the contents were completely mixed. The tubes were incubated at room temperature for 5 minutes, with occasional, gentle inverting to mix. After incubation, 1 mL of 'W5+ medium' was slowly added and the tubes were gently inverted 5-10 times. The tubes were then centrifuged at 1500 rpm for 5 minutes in a microcentrifuge (Eppendorf). The supernatant was carefully removed making sure not to disturb the pellet. Once the supernantant was removed, 1 mL of 'WI medium' (4 mM MES [pH6.0], 1 mL of 0.2 mM MES [pH6.0], 0.6 M mannitol, 30 mL 1M mannitol, 20 mM KCl, 5 mL 0.2M KCl and 14 mL water) was added to each tube and gently inverted to resuspend the pellet. The tubes were then covered with aluminum foil to eliminate lighting and placed on their side for overnight incubation after which genomic DNA was extracted and analyzed for targeted genome modification.

The foregoing demonstrates an example of the disclosed method for the targeted modification, e.g., site-specific integration, of a haploid maize genome in protoplasts isolated from microspore-derived callus which were transformed with a donor polynucleotide and a polynucleotide encoding a zinc finger nuclease (ZFN).

Example 5. Molecular Analysis of Haploid Protoplasts with Targeted Genome Modification Asymmetric nested in-out PCR (ANIO) (U.S. Provisional App. No. 61/873,719) was used to detect targeted genome modification in genomic DNA extracted from transfected protoplasts of Example 4. Sets of primer pairs used for detection are shown in Table 3. One pair of primers was designed to bind specifically to the genomic sequence and the other pair of primers was designed to bind donor polynucleotide DNA sequence. After initial denaturing, the amplification program included: 98° C. for 12 seconds and 66° C. for 30 seconds for 15 cycles and then a 72° C. for 10 minutes with a final hold at 4° C. using the EX-TAQ HS™ PCR kit (Clontech Laboratories, Inc.; Mountain View, California, USA). The first PCR product was then used in a nested, second PCR reaction. After the initial denaturing of the first PCR product, the amplification program included: 98° C. for 12 seconds, 66° C. for 30 seconds and then 68° C. for 1 minute for 30 cycles and then a 72° C. for 10 minutes followed by a final hold at 4° C. The PCR products were resolved by gel electrophoresis using a 1% E-gel™ (Invitrogen, Carlsbad, CA). The results of electrophoresis produced the expected gel fragment sizes for the PCR products (700 and 1053 bp, respectively, for the 5' and 3' junctions) indicating the presence of a targeted insertion. Thus, the foregoing indicates that the disclosed method produced targeted insertion of the donor polynucleotide transgene in the maize haploid genome.

TABLE 3

| Primers used for ANIO PCR reactions. | | |
|---|---|---|
| Primer Name | SEQ ID NO: | Sequence |
| APL02-5PriF1 | SEQ ID NO: 3 | CGCCACAAATCTG AACCAGCA |
| Spec-PriR1 | SEQ ID NO: 4 | CCACGATCGACAT TGATCTGGCTA |
| APL02-5nstPriF1 | SEQ ID NO: 5 | CCAGCATACAGTT AGGGCCCA |
| Spec-nstPriR1 | SEQ ID NO: 6 | GTTGCCTTGGTAG GTCCAGC |
| APL02-3PriR1 | SEQ ID NO: 7 | GCGACATATCAGG CCAACAGG |
| Uzi-PriF1 | SEQ ID NO: 8 | GGGATATGTGTCC TACCGTATCAGG |
| APL02-3nstPriR1 | SEQ ID NO: 9 | CGAAAACTCAGCA TGCGGGAA |
| Uzi-nstPriF1 | SEQ ID NO: 10 | GAGCCATCAGTCC AACACTGC |

The foregoing demonstrates an example of the disclosed method for confirming the targeted integration of donor polynucleotide into the genome of maize microspore-derived haploid tissue.

Example 6. Constructs for Targeted Genome Modification of Haploid Callus

Figure 3:
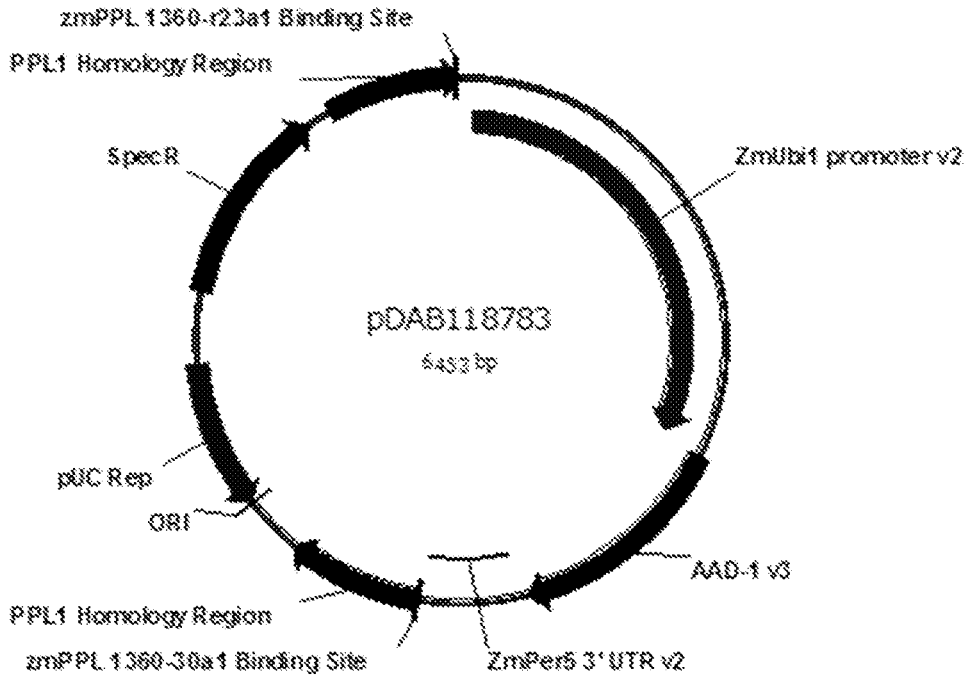
FIG. 3 provides a plasmid map of pDAB118783. This plasmid map is of a donor construct for targeted aad-1 integration within a specific genomic locus of haploid callus cells.

For targeted transgene integration into haploid callus, a donor construct, pDAB118783, was used which contains ~500 bp of sequence homologous to that flanking the unique zmPPL_1360-r23a1 and zmPPL_1360-30a1 recognition sequences in the maize genome (FIG. 3). These sequences are referred to as 'Homology Arms'. This donor construct also contains an aad-1 expression cassette for in vitro selection on haloxyfop-containing media. The aad-1 gene expression is controlled by the maize ubil promoter and terminated by the maize per5 3' UTR. Co-delivery of this construct with pDAB111879 (ZFN construct) results in double strand genomic DNA cleavage at a unique genomic sequence as a result of ZFN expression. The 'Homology Arms' provide a template for homology-directed repair thereby integrating the aad-1 expression cassette into the genomic cleavage site.

The foregoing provides examples of a donor polynucleotide (pDAB118783) which comprises a selectable marker transgene, aad1, and is suitable for use in the disclosed method of modifying a haploid maize genome by targeted integration of the transgene into the haploid genome.

Example 7. Targeted Genome Modification in Haploid Callus

Three days prior to bombardment, haploid callus was minced into ~1-2 mm pieces using a disposable scalpel, placed onto the surface of fresh 'callus medium' and incubated in the dark at 28° C. About 4 hours prior to bombardment, callus pieces were arranged in a 1 cm diameter circle in the center of a 100×15 mm Petri™ dish containing 'osmotic medium' ('callus medium' with the addition of 45.5 g/L each of sorbitol and mannitol) and incubated in the dark at 28° C. Callus was bombarded with a total of 0.5 µg of DNA (either pDAB111879 [ZFN] only or a 10:1 combination of pDAB118783 [Donor] and pDAB111879 [ZFN]) precipitated with 2.5 M CaCl$_2$ and 0.1 M spermidine onto the surface of 150 µg of 0.6µ gold at 900 psi and 6 cm flight distance using a PDS-1000 particle acceleration Device™ (BioRad; Hercules, California, USA).

The foregoing demonstrates an example of the disclosed method for the targeted modification of haploid maize genome by microparticle bombardment of microspore-derived haploid callus with a ZFN and donor polynucleotide.

Example 8. Molecular Analysis of Haploid Callus with Targeted Genome Modification Samples of callus tissue transformed with pDAB111879 (ZFN) only by microparticle bombardment in Example 7 were lyophilized for genomic DNA extraction using the Qiagen (Germantown, Maryland, USA) plant DNA extraction Kit™ according to manufacturer's specifications. Genomic DNA was resuspended in 200 µL of water and concentration was determined by Nanodrop® (Invitrogen, Carlsbad, California, USA). Integrity of the DNA was estimated by running all samples on 0.8% agarose E-gels™ (Invitrogen). All samples were normalized (25 ng/µL) for PCR amplification to generate amplicons for sequencing using a system from Illumina® (San Diego, California).

For preparative PCR, 5 µL from each rep was pooled and 5-individual small scale PCR reactions were performed for each template using 0.2 µM appropriate bar-coded primers, Accuprime Pfx Supermix® (Invitrogen) and 25 ng of template genomic DNA in a 24 µL reaction. Cycling parameters included initial denaturation at 95° (5 minutes) followed by 35 cycles of denaturation (95° C., 15 seconds), annealing (55° C., 30 seconds), extension (68° C., 1 minutes) and a final extension (72° C., 7 minutes). The PCR products were pooled together and gel purified on 4% agarose gels using Qiagen MinElute™ gel extraction/purification kit. Concentrations of the gel purified amplicons were determined and PCR amplicon samples were prepared by pooling approximately 200 ng of bar-coded amplicons from ZFN targeted and corresponding wild type controls (Table 4).

TABLE 4

Primers used for amplification of
genomic target sequence.

| Experiment | Name | SEQ ID NO: | Sequence |
|---|---|---|---|
| Control | 211YF | SEQ ID NO: 11 | F-tacgtaTGGCACT AATCTCACCGGCT |
| | 211YR | SEQ ID NO: 12 | R-tacgtaAGTCTTA GAAGTACGCTACCGT |
| Treated | 221F | SEQ ID NO: 13 | F-acgtacTGGCACT AATCTCACCGGCT |
| | 221R | SEQ ID NO: 14 | R-acgtacAGTCTTA GAAGTACGCTACCGT |

Illumina® sequencing was performed and analyzed using a sequence analysis script. Low quality sequences (sequences with a quality score cut off <5) were filtered out and the remaining sequences were parsed according to barcodes. The bar code directories were then aligned with the reference sequence and scored for insertions and/or deletions. Cleavage activity was detected as a function of high quality sequences with insertions and/or deletions resulting from error-prone NHEJ repair. A representative set of altered sequences (SEQ ID NO:33 to SEQ ID NO:45) are provided as an alignment to the genomic DNA target sequence (SEQ ID NO:32) to show the resulting deletions and additions (FIG. 4). A summary of the frequencies are shown in Table 5.

TABLE 5

Insertion-deletion (Indel) frequency at the PPL1 locus in
bombarded vs. control callus.

| Treatment | High Quality Reads | Total Indels After Background Correction | Indels per 1 Million High Quality Reads |
|---|---|---|---|
| Control | 33,278,757 | 167 | 5.0 |
| ZFN | 22,047,031 | 883 | 40.0 |

Thus, the foregoing indicates that the disclosed method produced targeted mutagenesis at the PPL1 locus of the maize haploid genome. The foregoing also demonstrates an example of the disclosed method for confirming targeted mutagenesis of the haploid genome.

Example 9. Chromosome Doubling, Selection and Plant Regeneration of Haploid Callus Callus from Example 7 co-bombarded with pDAB118783 (donor) and pDAB111879 (ZFN) was transferred the next morning onto the surface of filter paper (Whatman #4) placed over the surface of a 100×25 Petri™ dish containing fresh 'callus medium', soaked with 1 mL of 0.025% colchicine solution and incubated in the dark at 28° C. After 48 hours, the colchicine-treated callus was rinsed with 4 mL of liquid 'callus medium' using a 100µ cell strainer (Falcon 352360), blotted dry on sterile filter paper and transferred to 100×20 mm Petri™ dishes containing fresh 'callus medium'. After an additional 4 days (8 days post-bombardment) in the dark at 28° C., the doubled haploid nature of the callus was confirmed by flow cytometer, the results of which are shown in FIG. 5. The callus was then transferred to 'selection medium' ('callus medium' with 100 µM Haloxyfop™.

After 14 days on 'selection medium', the callus was transferred to fresh 'selection medium' for an additional 14 days and placed in low light at 28° C. After a total of 4 weeks on 'selection medium' (5 weeks from bombardment), the callus was transferred to 100×25 mm Petri™ dishes containing 'pre-regeneration medium' (MS salts and vitamins, 45 g/L sucrose, 350 mg/L L-proline, 250 mg/L MES, 100 mg/L myo-inositol, 2.5 mg/L ABA, 1 mg/L BAP, 0.5 mg/L NAA, 1 mg/L silver nitrate, 2.5 g/L Gelrite™ with 100 µM haloxyfop adjusted to pH 5.8) and placed in the light (50 µM) at 28° C. After 7 days, the callus was transferred to a PhytaTray™ II (Sigma-Aldrich; St. Louis, Missouri, USA) containing 'regeneration medium' (MS salts and vitamins, 60 g/L sucrose, 100 mg/L myo-inositol, 2.5 g/L Gelrite™ with 100 µM Haloxyfop™ for pDAB118873+ pDAB111879] adjusted to pH 5.8) and placed in the light (160 µM) at 28° C. After 14-21 days, shoots are transferred to 'shoot elongation medium' (MS salts, N6 vitamins, 30 g/L sucrose, 500 mg/L MES, 5.5 g/L agar with 100 µM Haloxyfop™ adjusted to pH 5.8) and placed in the light (190 µM) at 28° C.

Rooted plants were transplanted into 10 cm plastic pots containing Pro-Mix BX™ (Premier Tech; Riviere-du-Loup, Canada) and placed in a growth chamber (Conviron; Winnipeg, Canada) with a 16/8 hr photoperiod and temperatures of 27/24° C. Plants were then transplanted to 5 gallon pots containing a mixture of 95% Pro-Mix BX™ and 5% clay/loam soil and transferred to a greenhouse with supplemental lighting provided by metal halide and high-pressure sodium lamps with a 16/8 hr photoperiod and temperatures of 30/20° C. Plants were then grown to maturity and self-pollinated.

The foregoing demonstrates an example of the disclosed method for regenerating a doubled haploid plant from microspore-derived haploid callus that comprises a targeted transgene integrated into its genome.

Example 10. Molecular Analysis of Doubled Haploid Transgenic Plants

Tissue samples of the double haploid plants of Example 9 were collected in 96-well collection plates and lyophilized for 2 days. Tissue maceration was performed with a Genogrinder 2010™ (SPEX Sample Prep) and stainless steel beads. Following tissue maceration genomic DNA was isolated in high throughput format using the BioSprint Kit™ (Qiagen; Germantown, Maryland, USA) according to the manufacturer's suggested protocol. Genomic DNA was quantified by Quant-IT Pico Green DNA assay Kit™ (Molecular Probes; Invitrogen; Carlsbad, California, USA). Quantified genomic DNA was adjusted to 2 ng/µL for the hydrolysis probe assay using a Biomek NXP™ automated liquid handler (Beckman Coulter; Pasadena, California, USA).

Transgene copy number determination by hydrolysis probe assay was performed by real-time PCR using the LIGHTCYCLER®480 system (Roche Applied Science; Indianapolis, Indiana, USA). Assays were designed for aad-1 and the internal reference gene, invertase (Genbank Accession No: U16123.1) using LIGHTCYCLER® Probe Design Software 2.0. For amplification, LIGHTCYCLER® 480 Probes Master mix (Roche Applied Science) was prepared at 1× final concentration in a 10 µL volume multiplex reaction containing 0.4 µM of each primer and 0.2 µM of each probe (Table 6). A two-step amplification reaction was performed with an extension at 60° C. for 40 seconds for aad-1/invertase with fluorescence acquisition. Analysis of real time PCR data was performed using LIGHTCYCLER® software release 1.5 using the relative quant module and is based on the ∆∆Ct method. For this, a sample of gDNA from a single copy calibrator and known 2 copy check was included in each run.

TABLE 6

| Primer and probe information for hydrolysis probe assay of aad-1 and internal reference (invertase). | | | |
|---|---|---|---|
| Primer Name | SEQ ID NO: | Sequence | Detec-tion |
| GAAD1F | SEQ ID NO: 15 | 5' TGTTCGGTTCCCTC TACCAA 3' | — |
| GAAD1R | SEQ ID NO: 16 | 5' CAACATCCATCACCTTGA CTGA 3' | — |
| GAAD1P | SEQ ID NO: 17 | 5' FAM-CACAGAACCGTCGCTTC AGCAACA 3' | FAM |
| IVF-Taq | SEQ ID NO: 18 | 5' TGGCGGACGACGACTTGT 3' | — |
| INR-Taq | SEQ ID NO: 19 | 5' AAAGTTTGGAGGCTGCCGT 3' | — |
| IV-Probe | SEQ ID NO: 20 | 5' HEX-CGAGCAGACCGCCGTGTA CTTCTACC 3' | HEX |

The detection of events with targeted transgene insertion was performed using individual 'in-out' PCR reactions. The primer pairs, one specific to the flanking genomic sequence and the other specific to the donor construct that were used for detection are shown in Table 7. After the initial denaturing, the amplification program included: 94° C. for 30 s, 60° C. for 30 s, 72° C. for 1 m for 35 cycles, followed by 72° C. for 10 min before finally being held at 4° C. PCR reactions used the EX-TAQ PCR Kit™ (Clontech Laboratories, Inc). PCR products were resolved and identified using a 1% agarose gel.

TABLE 7

| Primers for In-out PCR reactions. | | |
|---|---|---|
| Primer Name | SEQ ID NO: | SEQUENCE |
| MAS863 | SEQ ID NO: 21 | 5' AAGCGGTGCGTTGGTATTAG 3' |
| MAS872 | SEQ ID NO: 22 | 5' GCGTTTAACAGGCTGGC 3' |
| MAS873 | SEQ ID NO: 23 | 5' CGATGCTCACCCTGTTGTTTG 3' |
| MAS864 | SEQ ID NO: 24 | 5' TCGCATACGACGGGCAT 3' |

ZFN-mediated disruption of the cleavage site was determined by a hydrolysis probe assay via real-time PCR using the LIGHTCYCLER® 480 system (Roche Applied Science). Assays were designed to have the primers and probe anneal to sequences flanking the ZFN binding site and the internal reference invertase. For amplification, LIGHTCY- CLER® 480 Probe Master mix was prepared at 1× final concentration in a 10 μL volume multiplex reaction containing 0.4 μM of each primer and 0.2 μM of each probe (Table 8). A two-step amplification reaction is performed with an extension at 60° C. for 30 seconds with fluorescence acquisition. Analysis of real time PCR data was performed with LIGHTCYCLER® software release 1.5 using the relative quant module and comparing the target to reference ratio. A sample of genomic DNA from a non-transgenic control plant was included in each run.

TABLE 8

| Primer and probe information for hydrolysis probe assay of genomic locus disruption. | | | |
|---|---|---|---|
| Primer Name | SEQ ID NO: | Sequence | Detec-tion |
| MAS706 | SEQ ID NO: 25 | 5' ATAAGACATCGAGCTAGT GTAAGCGTAGGC 3' | — |
| MAS707N | SEQ ID NO: 26 | 5' TCACAACTGTTTAGGCGT GTCCTCTTAA 3' | — |
| MAS708 | SEQ ID NO: 27 | 5' FAM-AAAGCTGCAGCTGC CTGTTCCCTGTAC_IB_ZEN 3' | FAM |
| MAS861 | SEQ ID NO: 28 | 5' CAAATAAGACATCGAGCT AGTGTAAG 3' | — |
| MAS862 | SEQ ID NO: 29 | 5' CTGTTTAGGCGTGTCCTCTT 3' | — |

T₀ double haploid maize plants which contained a targeted aad-1 construct as determined via 'in-out' PCR and locus disruption qPCR assay were selected for Sothern blots analysis. Southern blots were made and probed as previous described. The samples were then digested using HindIII (New England BioLabs, Ipswich, MA) overnight at 37° C. The probe was generated using the primers shown in Table 9, which bind to the genomic sequence outside of the 'homology arms'. The resulting Southern blots confirmed that the transgenic events contained a full length copy of the targeted aad-1 construct.

TABLE 9

| Primers used to make probe for Southern blot analysis. | | |
|---|---|---|
| Primer Name | SEQ ID NO: | Sequence |
| MAS864 | SEQ ID NO: 30 | 5' TCGCATACGACGGGCAT 3' |
| MAS865 | SEQ ID NO: 31 | 5' TGGCAGCCGGTGCGA 3' |

The foregoing demonstrates several examples of the disclosed method for confirming that doubled haploid plants (regenerated from microspore-derived haploid callus) displayed targeted transgene integration.

What is claimed is:

1. A method for modifying a maize genome by site-specific nuclease targeted mutagenesis, by a zinc finger nuclease, the method comprising:

(a) crossing an elite maize line with a different maize line having high microspore culture response to produce a hybrid maize line having elite performance characteristics and high microspore culture response;

(b) producing a microspore derived, transformation competent callus tissue from the progeny of the hybrid maize derived from crossing an elite maize line with a different maize line having high microspore culture response;

(c) isolating a maize microspore-derived, transformation-competent haploid callus comprising a paternal haploid tissue genome from the tissue of the progeny of the hybrid maize line, wherein the callus is assayed and determined to be haploid;

(d) delivering a polynucleotide encoding a site-specific nuclease to the transformation-competent haploid callus resulting in the double strand cleavage of the haploid genome of the callus via particle bombardment; and, (e) confirming that the haploid callus genome is modified by the encoded site-specific nuclease, wherein the site-specific nuclease's targeting specificity has been engineered to target the modified genomic sequence with at least an 8-fold increased level of targeted mutagenesis as compared to non-transformed callus.

2. The method of claim 1, wherein the method further comprises:

(f) delivering a donor polynucleotide and stably integrating the donor polynucleotide in the modified haploid callus genome.

3. The method of claim 2, wherein the donor polynucleotide comprises one or two domains and each domain is at least 85% identical to a sequence in the genomic DNA target region of the haploid callus genome.

4. The method of claim 1, wherein the method comprises confirming that the haploid callus genome is modified by performing a PCR based assay, Southern blot assay, Northern blot assay, protein expression assay, Western blot assay, ELISA assay, or Next Generation Sequencing assay.

5. The method of claim 1, wherein the method further comprises:

(g) treating the haploid callus comprising the modified haploid callus genome with a chromosome doubling agent;

(h) producing dihaploid maize tissue comprising a modified dihaploid maize genome; and, (i) regenerating the dihaploid maize tissue into a dihaploid maize plant comprising a homozygous modified dihaploid maize genome.

6. The method of claim 2, wherein the method further comprises:

(g) treating the haploid callus comprising the modified haploid tissue genome with a chromosome doubling agent;

(h) producing dihaploid maize tissue comprising a modified dihaploid maize genome; and, (i) regenerating the dihaploid maize tissue into a dihaploid maize plant comprising a homozygous modified dihaploid maize genome.

7. The method of claim 2, wherein the method further comprises:

(j) stably integrating the donor polynucleotide into a target region of the haploid tissue genome; and, (k) confirming that the donor polynucleotide integrated into the target region of the haploid tissue genome.

8. The method of claim 7, wherein the integrated donor polynucleotide is expressed within the maize haploid tissue.

9. The method of claim 7, wherein the integrated donor polynucleotide imparts an agronomic trait.

10. The method of claim 1, wherein the method further comprises:

(l) expressing the site-specific nuclease and introducing a mutation into the haploid genome of maize; and, (m) confirming that the haploid maize genome comprises a mutation.

11. The method of claim 2, wherein the method further comprises:

(n) treating the haploid callus comprising the stably integrated donor polynucleotide in the modified haploid callus genome with a chromosome doubling agent;

(o) producing dihaploid maize tissue comprising stably integrated donor polynucleotide in its dihaploid maize genome; and, (p) regenerating the dihaploid maize tissue into a dihaploid maize plant that is homozygous for the stably integrated donor polynucleotide.

12. The method of claim 11, further comprising:

(q) crossing the dihaploid maize plant with plants of a different parent maize line to produce F1 progeny plants;

(r) selecting one or more F1 progeny plants having the genome modification introduced by the encoded site-specific nuclease to produce one or more maize progeny plants comprising the modification introduced by the encoded site-specific nuclease; and, (s) optionally, (i) back-crossing F1 progeny plants with the dihaploid maize plant of claim 11 or the different parent maize line to produce backcross progeny plants, (ii) selecting for backcross progeny plants that comprise the genome modification introduced by the encoded site-specific nuclease, and (iii) further optionally repeating steps (i) and (ii) to produce one or more maize progeny plants comprising the modification introduced by the encoded site-specific nuclease.

* * * * *